(12) United States Patent
Lieberman et al.

(10) Patent No.: US 7,943,589 B2
(45) Date of Patent: May 17, 2011

(54) SIRNA MICROBICIDES FOR PREVENTING AND TREATING DISEASES

(75) Inventors: Judy Lieberman, Brookline, MA (US); Deborah Palliser, Cambridge, MA (US); David Knipe, Auburndale, MA (US)

(73) Assignees: President and Fellows of Harvard College, Cambridge, MA (US); Immune Disease Institute, Inc., Boston, MA (US)

( * ) Notice: Subject to any disclaimer, the term of this patent is extended or adjusted under 35 U.S.C. 154(b) by 330 days.

(21) Appl. No.: 11/916,334

(22) PCT Filed: Jun. 5, 2006

(86) PCT No.: PCT/US2006/021758
§ 371 (c)(1), (2), (4) Date: Feb. 15, 2008

(87) PCT Pub. No.: WO2006/133099
PCT Pub. Date: Dec. 14, 2006

(65) Prior Publication Data
US 2009/0022783 A1    Jan. 22, 2009

Related U.S. Application Data

(60) Provisional application No. 60/687,216, filed on Jun. 3, 2005.

(51) Int. Cl.
*A61K 31/70* (2006.01)
*C07H 21/04* (2006.01)
*C07H 21/02* (2006.01)
*C12Q 1/68* (2006.01)

(52) U.S. Cl. .................. 514/44 A; 536/23.1; 536/24.1; 536/24.5; 435/6; 435/375

(58) Field of Classification Search .............. None
See application file for complete search history.

(56) References Cited

U.S. PATENT DOCUMENTS

| | | | | |
|---|---|---|---|---|
| 5,248,670 A | * | 9/1993 | Draper et al. | 514/44 A |
| 5,514,577 A | * | 5/1996 | Draper et al. | 435/238 |
| 5,658,891 A | * | 8/1997 | Draper et al. | 514/44 A |
| 6,310,044 B1 | * | 10/2001 | Draper et al. | 514/44 A |
| 6,821,519 B2 | * | 11/2004 | Day et al. | 424/231.1 |
| 7,358,068 B2 | * | 4/2008 | Vaillant et al. | 435/91.1 |
| 7,696,179 B2 | * | 4/2010 | Lieberman et al. | 514/44 R |
| 2003/0165476 A1 | | 9/2003 | Orson et al. | |
| 2003/0165820 A1 | | 9/2003 | Day et al. | |
| 2006/0293271 A1 | * | 12/2006 | McSwiggen et al. | 514/44 |

FOREIGN PATENT DOCUMENTS

| | | |
|---|---|---|
| GB | 2153686 A | 8/1985 |
| WO | 99/49067 A1 | 9/1999 |
| WO | 0176624 A1 | 10/2001 |
| WO | 02094185 A2 | 11/2002 |
| WO | 2004062591 A2 | 7/2004 |
| WO | 2005042705 A2 | 5/2005 |
| WO | 2005042716 A2 | 5/2005 |

OTHER PUBLICATIONS

Schultz et al., Investigative Opthalmology & Visual Science vol. 45. suppl.[1], p. U596, 2004, E abrasct 1651(2 pages).*

* cited by examiner

*Primary Examiner* — Sean R McGarry
(74) *Attorney, Agent, or Firm* — Nixon Peabody LLP

(57) ABSTRACT

The invention provides a microbicidal composition comprising at least one siRNA. The siRNA is an RNA duplex made of one or two molecules. A portion of the siRNA is identical to a target sequence in an essential gene of a virus. The virus may be a herpesvirus, for example, HSV-1 or HSV-2. Preferably, the herpesvirus is HSV-2. The microbicidal composition further comprises a pharmaceutically acceptable carrier. Also included in the invention are methods to prevent and treat viral infections by administration of the microbicidal composition. Preferably, the microbicidal composition is administered transmucosally.

17 Claims, 3 Drawing Sheets

SIRNA MICROBICIDES FOR PREVENTING AND TREATING DISEASES

CROSS-REFERENCE

This application is a National Phase Entry Application under 35 U.S.C. §371 of co-pending International Application PCT/US2006/021758 filed 5 Jun. 2006, which designated the U.S. and which claims benefit under 35 U.S.C. §119(e) of U.S. Provisional Application Ser. No. 60/687,216, filed on Jun. 3, 2005, the content of which is relied upon and incorporated herein by reference in its entirety.

GOVERNMENT SUPPORT

This invention was supported, in part, by National Institutes of Health (NIH) Grant No. R21 AI058695 and R01 AI057552. The government of the United States has certain rights to the invention.

BACKGROUND OF THE INVENTION

Two well known species of human disease-causing herpes simplex viruses are herpes simplex virus type 1 (HSV-1) and its close cousin, herpes simplex virus type 2 (HSV-2), collectively HSV. At the molecular level, HSV-1 and HSV-2 share approximately 50% of their DNA. Both types infect the body's mucosal surfaces, usually the mouth or genitals, and then establish latency in the nervous system. For both HSV-1 and HSV-2 infections, at least two-thirds of infected people have no symptoms, or symptoms too mild to notice. However, both types can recur and spread even when no symptoms are present.

Moreover, prior infection with another STD, such as HSV 2, predisposes an individual to a higher risk of contracting HIV. In the U.S. alone, up to 25% of the population is seropositive for HSV 2. This figure rises to 80% in sub-Saharan Africa, where HIV is endemic. Viral reactivation of HSV occurs in >95% of healthy individuals and leads to the formation of genital ulcerations, resulting in destruction of the mucosal barrier and an influx of activated CD4+ T cells-optimal conditions for HIV infection. Therefore, decrease in HSV 2 infection could lead to a significant drop in HIV infection rates.

Since vaccines giving mucosal protection are probably many years away and condoms, although highly effective in preventing infection by sexually transmitted disease (STD) causing microbes, have failed to become generally accepted by males in many parts of the world, protective means are required which are under the control of the woman and can, if necessary, be used without the knowledge or consent of the male partner. Vaginal microbicides would meet this requirement and could not only protect the female's reproductive tract against infectious agents transmitted by the male, but could also protect the male's genital mucosa against possible infectious agents from the female.

Accordingly, it would be desirable to develop new treatments for viral diseases in general and STDs in particular that can be used frequently without adverse effects.

SUMMARY OF THE INVENTION

The present invention is directed to methods of treating viral diseases using siRNAs as microbicides. The invention is based upon our findings in a murine model that an siRNA microbicide delivered vaginally prevents HSV infection. Accordingly, the present invention provides an isolated siRNA comprising a sense RNA strand and an antisense RNA strand or a single strand. The sense and the antisense RNA strands, or the single RNA strand, form an RNA duplex, and wherein the RNA strand comprises a nucleotide sequence having sufficient complementarity to a target sequence of about 15 to about 30 contiguous nucleotides in a viral RNA to direct cleavage of the viral RNA via RNA interference. Preferably, the virus is selected from the group consisting of orthomyxoviruses, e.g., influenza virus, paramyxoviruses, e.g., RSV, coronaviruses, adenoviruses, papillomaviruses, picornaviruses, e.g., rhinovirus and hepatitis A virus, hepadnaviruses, e.g., hepatitis B virus, flaviviruses, e.g., hepatitis C virus, retroviruses, e.g., HIV, HTLV-I and HTLV-II, poxviruses, e.g., MCV, herpesviruses, e.g., HSV-1, HSV-2, VZV-2, CMV, HHV-6, HHV-7, HHV-8, VZV-2, CMV, HHV-6, HHV-7, HHV-8 and EBV, or any combination thereof. Preferably, the virus is an STD causing virus. Preferably, the virus is HIV, HPV or HSV. More preferably, the virus is HSV. Preferably, the target sequence is an HSV gene. Essential HSV genes include, for example, UL5, UL27 and UL29.

In one embodiment, the siRNA is formulated with a pharmaceutically acceptable carrier to form a microbicidal composition that can treat or prevent viral infection by a virus noted above. Preferably, the viral infection is an STD. Preferably, the viral infection is mediated by HIV, HPV, or HSV. More preferably, the viral infection is mediated by HSV. Preferably, the microbicide is formulated for topical, particularly genital or rectal, administration. More preferably, the microbicide is formulated for delivery of the siRNA by lipofection.

In another embodiment, the present invention provides a method of inhibiting expression of viral mRNA, or preventing or treating viral mediated sexually transmitted disease (STD). Preferably, the disease is mediated by HSV. The method comprises administering an effective amount of siRNA of the invention to a subject having or at risk of developing an STD. Preferably, the siRNA is administered transmucosally, e.g., vaginally, rectally.

BRIEF DESCRIPTION OF THE FIGURES

FIG. 1c, Viral mRNA (UL5, black; UL27, dark gray; UL29, light gray; TK, white) relative to GAPDH was analyzed by quantitative RT-PCR using Vero cells treated and harvested as in FIG. 1b. Each of the antiviral siRNAs inhibited expression of all 4 viral genes, demonstrating inhibition of viral replication and spread.

FIGS. 2a-2b show siRNAs targeting HSV-2 protect mice from lethal HSV-2 vaginal infection. Mice given 500 pmoles lipid-complexed siRNA in the vaginal cavity 2 hr before and 4 hr after vaginal infection with ~2 LD50 HSV-2 were analyzed for survival (FIG. 2a) and vaginal viral shedding on day 6 (FIG. 2b). Pooled data from 3 independent experiments are shown in FIG. 2a. FIG. 2b, Disease groups are HSV only, circles; GFP siRNA, squares; UL27.2 siRNA, diamonds; UL29.2, triangles. Mice that survived after day 12 remained healthy. FIG. 2b, Vaginal viral shedding was quantified on day 6 after infection from viral swabs. Geometric mean viral titer for each group is shown by the bars. Mice treated with UL29.2 siRNA had significantly less viral shedding than mice that did not receive siRNA.

DETAILED DESCRIPTION OF THE INVENTION

Figure 1:
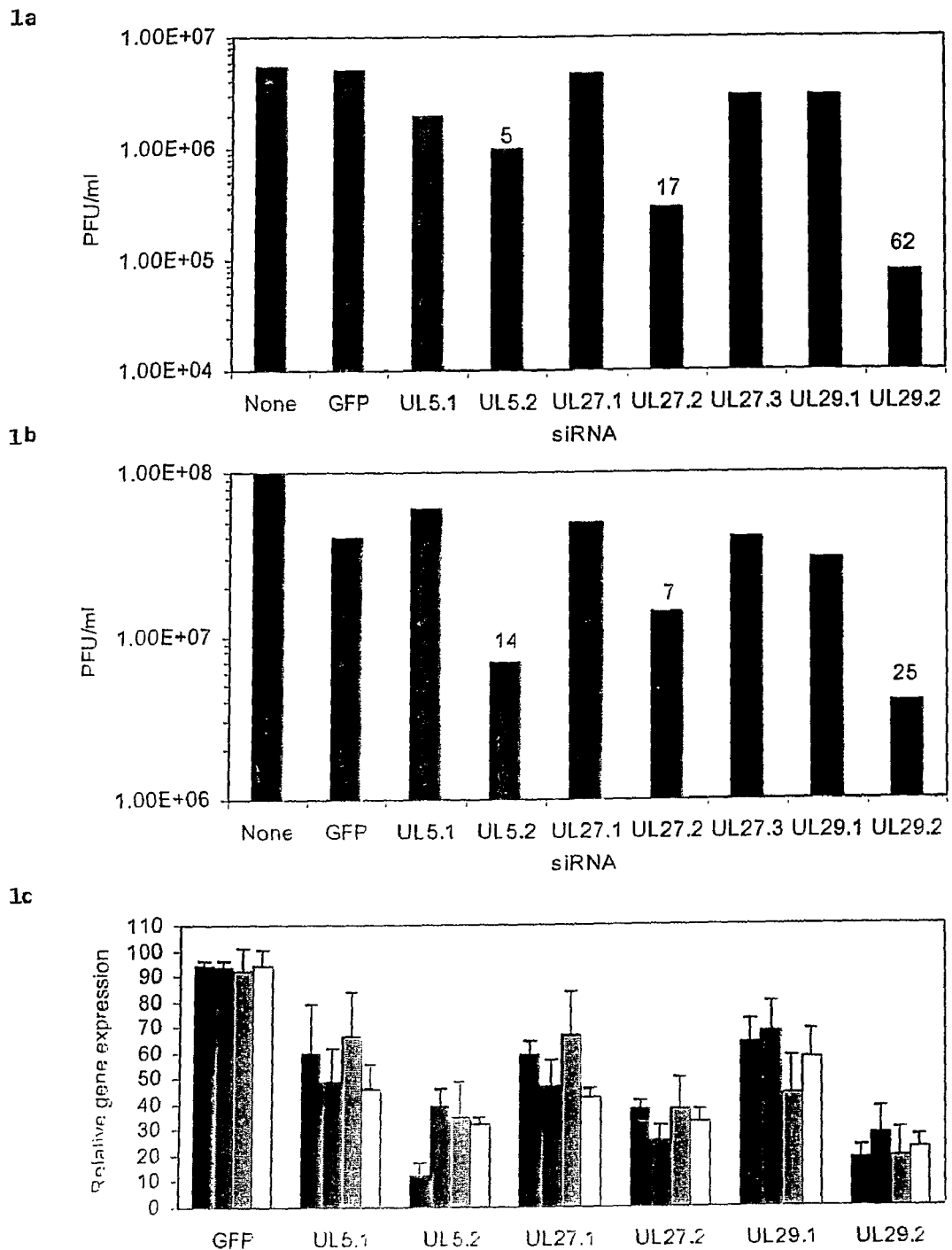
FIGS. 1a-1c show siRNAs targeting HSV reduce viral replication in vitro. NIH3T3 (FIG. 1a) or Vero (FIG. 1b) cells, transfected overnight with 100 pmoles siRNA were incubated with HSV 186kpn at MOI=1 for 1 hr and harvested 20 hrs later to analyze viral production by plaque assay. Values above bars for UL5.2, UL27.2 and UL29.2 show fold reduction.

The present invention is based on the surprising discovery that siRNAs designed to interfere with the expression of one or more essential genes of a virus may be delivered to a subject by means of lipid transfection agents. Delivery of the siRNAs designed to interfere with the expression of one or more essential genes of a virus successfully treat and/or prevent viral infection in the subject.

Accordingly, the present invention is directed to methods of treating and/or preventing viral infection using double-stranded siRNAs designed to interfere with the expression of essential viral genes. Preferably, the viral infection is mediated by a virus selected from the group consisting of orthomyxoviruses, e.g., influenza virus, paramyxoviruses, e.g., RSV, coronaviruses, adenoviruses, papillomaviruses, e.g., HPV, picornaviruses, e.g., rhinovirus and hepatitis A virus, hepadnaviruses, e.g., hepatitis B virus, flaviviruses, e.g., hepatitis C virus, retroviruses, e.g., HIV, HTLV-I and HTLV-II, poxviruses, e.g., MCV, herpesviruses, e.g., HSV-1, HSV-2, VZV-2, CMV, HHV-6, HHV-7, HHV-8, VZV-2, CMV, HHV-6, HHV-7, HHV-8 and EBV, or any combination thereof. More preferably, the viral infection is an HSV infection. More preferably, the HSV infection is an HSV-1 or HSV-2 infection.

The invention provides siRNAs, pharmaceutical compositions, e.g., microbicides, comprising the siRNAs, in vitro and in vivo methods of inhibiting expression of viruses, including HSV, and methods of treating and/or preventing viral infections, including HSV infection. "Microbicide" refers to a compound that can treat or prevent infections due to microbial agents, including viral infection, for example HSV infections. The invention further provides a device for delivery of the microbicide.

The invention provides an isolated siRNA comprising a sense RNA strand and an antisense RNA strand, or single RNA strand, wherein the sense and the antisense RNA strands, or the single RNA strand, form an RNA duplex, and wherein the RNA strand comprises a nucleotide sequence having sufficient complementarity to a target sequence of about 15 to about 30, preferably, about 19 to about 25, contiguous nucleotides in RNA from a virus for the siRNA to direct cleavage of said RNA via RNA interference. The viral RNA useful according to the invention refers to any known nucleic acid that is part of a viral genome and, in particular, nucleic acids comprising essential genes. More specifically, the siRNA inhibits expression of the target viral sequence. "Essential genes" refers to genes whose expression is required for infection and/or replication functions of the virus. The viral genome may be selected, for example, from the genomes of a virus noted above. Essential genes in the genomes of the viruses noted above are known to the skilled artisan. For example, the E6 and E7 genes in HPV. For example, the env, gag, pol, rev, nef, tat, vpr, as well as the non-coding LTRs in HIV. For example, sequences identified as GenBank ID Nos. NC_001806 and NC_001798 are useful in the present invention for determining siRNA target sequences of HSV. In one embodiment, the essential genes are HSV-1 (GenBank NC_001806) gB/UL27 (complement of bases 53058-56080), glycoprotein D/US6 (bases 138309-141048), and UL29 genes (complement of 58463-62053). In one embodiment, the essential genes are HSV-2 (GenBank NC_001798) glycoprotein D/US6 (bases 141016-142197), UL5 (complement of bases 12604-15249), UL27 (complement of bases 56117-53403 of NC_001798), and UL29 genes (complement of bases 62447-58857). In one preferred embodiment, the siRNA target sequences are directed to the UL5 gene, coding for a component of the DNA helicase-primase complex (complement of bases 12604-15249 of NC_001798); UL27 gene, coding for a glycoprotein (complement of bases 56117-53403 of NC_001798); UL29 gene, coding for a single stranded binding protein (complement of bases 62447-58857). In one embodiment, the essential gene is the HSV Latency Associated Transcript (LAT gene), including the miRNA generated from exon 1 of the LAT gene (see, e.g., Gupta et al. "Anti-apoptotic function of a microRNA encoded by the HSV-1 latency-associated transcript" Nature, advance online publication 31 May 2006). In yet another embodiment, the siRNAs are selected from the sequences listed in Table 1.

TABLE 1

| Target Sequense | Seq ID | Sense strand | Seq ID | Antisense strand | Seq ID |
|---|---|---|---|---|---|
| CTACGGCATCAGCTCCAAA | 1 | CUACGGCAUCAGCUCCAAA | 1 | UUUGGAGCUGAUGCCGUAG | 2 |
| TGTGGTCATTGTCTATTAA | 3 | UGUGGUCAUUGUCUAUUAA | 3 | UUAAUAGACAAUGACCACA | 4 |
| GTTTACGTATAACCACATA | 5 | GUUUACGUAUAACCACAUA | 5 | UAUGUGGUUAUACGUAAAC | 6 |
| ACGTGATCGTGCAGAACTC | 7 | ACGUGAUCGUGCAGAACUC | 7 | GAGUUCUGCACGAUCACGU | 8 |
| TCGACCTGAACATCACCAT | 9 | UCGACCUGAACAUCACCAU | 9 | AUGGUGAUGUUCAGGUCGA | 10 |
| CTTTCGCAATCAATTCCAA | 11 | CUUUCGCAAUCAAUUCCAA | 11 | UUGGAAUUGAUUGCGAAAG | 12 |
| CCACTCGACGTACTTCATA | 13 | CCACUCGACGUACUUCAUA | 13 | UAUGAAGUACGUCGAGUGG | 14 |

Short Interfering RNAs (siRNAs)

"Short interfering RNA" (siRNA), also referred to herein as "small interfering RNA" is defined as an agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15, 16, 17, 18, 19, 20, 21, 22, 23, 24, 25, 26, 27, 28, or 30 nucleotides in length, preferably about 15 to about 28 nucleotides, more preferably about 19, 20, 21, 22, 23, 24, or 25 nucleotides in length, and more preferably about 19, 20, 21, 22, or 23 nucleotides in length, and may contain a 3' and/or 5' overhang on each strand having a length of about 0, 1, 2, 3, 4, or 5 nucleotides. The length of the overhang is independent between the two strands, i.e., the length of the over hang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety).

In one embodiment, the siRNA of the present invention comprises two molecules where the sense RNA strand comprises one RNA molecule, and the antisense RNA strand comprises one RNA molecule; or the sense and antisense RNA strands forming the RNA duplex may be covalently linked by a single-stranded hairpin.

Synthetic siRNA molecules, including shRNA molecules, of the present invention can be obtained using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g., Elbashir, S. M. et al. (2001) *Nature* 411:494-498; Elbashir, S. M., W. Lendeckel and T. Tuschl (2001) *Genes & Development* 15:188-200; Harborth, J. et al. (2001) *J. Cell Science* 114:4557-4565; Masters, J. R. et al. (2001) *Proc. Natl. Acad. Sci., USA* 98:8012-8017; and Tuschl, T. et al. (1999) *Genes & Development* 13:3191-3197). Alternatively, several commercial RNA synthesis suppliers are available including, but not limited to, Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). As such, siRNA molecules are not overly difficult to synthesize and are readily provided in a quality suitable for RNAi. In addition, dsRNAs can be expressed as stem loop structures encoded by plasmid vectors, retroviruses and lentiviruses (Paddison, P. J. et al. (2002) *Genes Dev.* 16:948-958; McManus, M. T. et al. (2002) *RNA* 8:842-850; Paul, C. P. et al. (2002) *Nat. Biotechnol.* 20:505-508; Miyagishi, M. et al. (2002) *Nat. Biotechnol.* 20:497-500; Sui, G. et al. (2002) *Proc. Natl. Acad. Sci., USA* 99:5515-5520; Brummelkamp, T. et al. (2002) *Cancer Cell* 2:243; Lee, N. S., et al. (2002) *Nat. Biotechnol.* 20:500-505; Yu, J. Y., et al. (2002) *Proc. Natl. Acad. Sci., USA* 99:6047-6052; Zeng, Y., et al. (2002) *Mol. Cell.* 9:1327-1333; Rubinson, D. A., et al. (2003) *Nat. Genet.* 33:401-406; Stewart, S. A., et al. (2003) *RNA* 9:493-501). These vectors generally have a polIII promoter upstream of the dsRNA and can express sense and antisense RNA strands separately and/or as a hairpin structures. Within cells, Dicer processes the short hairpin RNA (shRNA) into effective siRNA.

The targeted region of the siRNA molecule of the present invention can be selected from an essential viral gene, e.g., an envelope glycoprotein or a DNA binding protein, beginning from about 25 to 50 nucleotides, from about 50 to 75 nucleotides, or from about 75 to 100 nucleotides downstream of the start codon. Nucleotide sequences may contain 5' or 3' UTRs and regions nearby the start codon. One method of designing a siRNA molecule of the present invention involves identifying the 23 nucleotide sequence motif AA(N19)TT (where N can be any nucleotide) and selecting hits with at least about 25%, 30%, 35%, 40%, 45%, 50%, 55%, 60%, 65%, 70% or 75% G/C content. The "TT" portion of the sequence is optional. Alternatively, if no such sequence is found, the search may be extended using the motif NA(N21), where N can be any nucleotide. In this situation, the 3' end of the sense siRNA may be converted to TT to allow for the generation of a symmetric duplex with respect to the sequence composition of the sense and antisense 3' overhangs. The antisense siRNA molecule may then be synthesized as the complement to nucleotide positions 1 to 21 of the 23 nucleotide sequence motif. The use of symmetric 3' TT overhangs may be advantageous to ensure that the small interfering ribonucleoprotein particles (siRNPs) are formed with approximately equal ratios of sense and antisense target RNA-cleaving siRNPs (Elbashir et al. (2001) supra and Elbashir et al. 2001 supra). Analysis of sequence databases, including but not limited to the NCBI, BLAST, Derwent and GenSeq as well as commercially available oligosynthesis companies such as OligoEngine, Inc. (Seattle, Wash.), may also be used to select siRNA sequences against EST libraries to ensure that only one gene is targeted.

The target gene or sequence of the siRNA is designed to be substantially homologous to the target sequence, or a fragment thereof. As used herein, the term "homologous" is defined as being substantially identical, sufficiently complementary, or similar to the target viral mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical to its target allele so as to prevent its interaction with the normal allele.

In one embodiment, only one siRNA that targets a viral target is used. The delivery or administration of the siRNA is preferably performed in free form, i.e. without the use of vectors. In another embodiment that is especially useful to prevent infection after viral contact, a mixture of siRNAs targeting either the same viral gene or at least 2, 3, 4, 5 or up to at least 10 different viral genes are used. In one embodiment, the siRNAs include one or more sequences listed in Table 1. Other siRNAs useful according to the methods of the present invention may be readily designed and tested.

The siRNAs used in the methods of the invention preferably target only one sequence. In one preferred embodiment, a mixture of siRNAs designed to inhibit expression of one or more viral sequences are used in combination. Each of the siRNAs, can be screened for potential off-target effects may be analyzed using, for example, expression profiling. Such methods are known to one skilled in the art and are described, for example, in Jackson et al. Nature Biotechnology 6:635-637, 2003. In addition to expression profiling, one may also screen the potential target sequences for similar sequences in the sequence databases to identify potential sequences which may have off-target effects. For example, according to Jackson et al. (Id.) 15, or perhaps as few as 11 contiguous nucleotides, of sequence identity are sufficient to direct silencing of non-targeted transcripts. Therefore, one may initially screen the proposed siRNAs to avoid potential off-target silencing using the sequence identity analysis by any known sequence comparison methods, such as BLAST. Design of siRNAs is known to the skilled artisan, see for example, Dykxhoorn & Lieberman 2006 "Running interference: prospects and obstacles to using small interfering rnas as small molecule drugs" Annu Rev Biomed Eng.

In conjunction with the present treatment methods, pharmacogenomics (i.e., the study of the relationship between an individual's genotype and that individual's response to a foreign compound or drug) may be considered. Differences in metabolism of therapeutics, including siRNAs, can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer one or more therapeutic siRNAs as described herein as well as tailoring the dosage and/or therapeutic regimen of treatment with an siRNA targeting a viral gene. For example, in one embodiment, before administering the siRNA to an individual, the target sequence of the viral strain harbored by the individual may be analyzed for any potential gene variations, such as polymorphisms or mutations, in the region against which the siRNA is targeted. For example, one may sequence the UL29 gene from the strain harbored by the individual. If one or more mutations or a polymorphisms is detected, the siRNA may be modified to target the specific mutant or polymorphic form of the target.

The siRNAs of the present invention are designed so as to maximize the uptake of the antisense (guide) strand of the siRNA into RNA-induced silencing complex (RISC) and thereby maximize the ability of RISC to target viral mRNA for degradation. This can be accomplished by looking for sequences that has the lowest free energy of binding at the 5'-terminus of the antisense strand. The lower free energy would lead to an enhancement of the unwinding of the 5'-end of the antisense strand of the siRNA duplex, thereby ensuring that the antisense strand will be taken up by RISC and direct the sequence-specific cleavage of the viral mRNA.

In one embodiment, at least one strand, alternatively both strands, of the RNA molecule has a 3' overhang from about 0 to about 6 nucleotides (e.g., pyrimidine nucleotides, purine nucleotides) in length. In other embodiments, the 3' overhang is from about 1 to about 5 nucleotides, from about 1 to about 3 nucleotides and from about 2 to about 4 nucleotides in length. In one embodiment the RNA molecule is double stranded, one strand has a 3' overhang and the other strand can be blunt-ended or have an overhang. In the embodiment in which the RNA molecule is double stranded and both strands comprise an overhang, the length of the overhangs may be the same or different for each strand. In a particular embodiment, the RNA of the present invention comprises about 19, 20, 21, or 22 nucleotides which are paired and which have overhangs of from about 1 to about 3, particularly about 2, nucleotides on both 3' ends of the RNA. The siRNA molecules of the present invention can also comprise a 3' hydroxyl group. In one embodiment, the 3' overhang is comprised of a dinucleotide of dithymidylic acid (TT) or diuridylic acid (uu). In one embodiment, the 3' overhangs can be stabilized against degradation. In another embodiment, both sense and antisense RNA strands of the siRNA may be stabilized against nuclease degradation. In a preferred embodiment, the RNA is stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly enhances the nuclease resistance of the overhang in tissue culture medium.

siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues may be used, such as a phosphorothioate linkage. The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatizes with a variety of groups.

In another aspect the nucleic acid molecules comprise a 5' and/or a 3'-cap structure. By "cap structure" is meant chemical modifications, which have been incorporated at either terminus of the oligonucleotide (see for example Wincott et al, WO 97/26270). These terminal modifications protect the nucleic acid molecule from exonuclease degradation, and can help in delivery and/or localization within a cell. The cap can be present at the 5'-terminus (5'-cap) or at the 3'-terminus (3'-cap) or can be present on both terminus. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., WO 97/26270).

In another embodiment the 3'-cap includes, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Iyer, 1993, Tetrahedron 49, 1925).

Other useful RNA derivatives incorporate nucleotides having modified carbohydrate moieties, such as 2'O-alkylated residues or 2'-O-methyl ribosyl derivatives and 2'-O-fluoro ribosyl derivatives. The RNA bases may also be modified. Any modified base useful for inhibiting or interfering with the expression of a target sequence may be used. For example, halogenated bases, such as 5-bromouracil and 5-iodouracil can be incorporated. The bases may also be alkylated, for example, 7-methylguanosine can be incorporated in place of a guanosine residue. Non-natural bases that yield successful inhibition can also be incorporated.

The most preferred siRNA modifications include 2'-deoxy-2'-fluorouridine or locked nucleic acid (LAN) nucleotides and RNA duplexes containing either phosphodiester or varying numbers of phosphorothioate linkages. Such modifications are known to one skilled in the art and are described, for example, in Braasch et al., Biochemistry, 42: 7967-7975, 2003. Most of the useful modifications to the siRNA molecules can be introduced using chemistries established for antisense oligonucleotide technology.

siRNA Delivery

Methods of delivering siRNA, e.g., siRNA of the present invention, or vectors containing siRNA of the present invention, to the target cells include delivery via lipofection reagent, delivery via transfection reagent, delivery via liposome, delivery via protein or polymer carriers, injection of a composition containing the siRNA or directly contacting the target cell with a composition comprising an siRNA. In another embodiment, an siRNA may be injected directly into any blood vessel, such as vein, artery, venule or arteriole, via, e.g., hydrodynamic injection or catheterization. Administration may be by a single injection or by two or more injections. Preferably, for treatment or prevention of STDs, the siRNA are delivered topically to the genital mucus membranes of the subject. One or more siRNAs may be used simultaneously.

As used herein, the term "target cell" is intended to refer to a cell, e.g., cervicovaginal epithelia, vaginal lamina propia, vaginal ectocervical mucosa, rectal epithelia, genital epithelia or mucosa, oral mucosa or epithelium, keratinocytes and epidermal cells, into which an siRNA molecule of the invention, including a recombinant expression vector encoding an siRNA of the invention, is introduced. The term "genital" is used herein to refer to areas of the body including the vagina, the vulva, the cervix, the anus, the rectum, the penis, the scrotum, the urethra, the internal regions housed by the penis and the scrotum, and all associated mucosal membranes. In one embodiment, the target cell is a neuronal cell, e.g., a cell in the sacral ganglia or a cell in the trigeminal ganglia. The terms "target cell" and "host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. Preferably, a target cell is a mammalian cell, e.g., a human cell.

In another preferred embodiment, the delivery is performed using an siRNA delivery system described in WO 06/023491, and U.S. Patent Application Publication No. 20040023902, incorporated herein by reference in their entirety. The method of targeted delivery both in vitro and in vivo of siRNAs into desired cells thus avoiding entry of the siRNA into other than intended target cells. The method allows treatment of specific cells with siRNAs limiting potential side effects of RNA interference caused by non-specific targeting of RNA interference. The method uses a complex or a fusion molecule comprising a cell targeting moiety and an siRNA binding moiety that is used to deliver the siRNA effectively into cells. For example, an antibody-protamine fusion protein when mixed with siRNA, binds siRNA and selectively delivers the siRNA into cells expressing an antigen recognized by the antibody, resulting in silencing of gene expression only in those cells that express the antigen. The siRNA or RNA interference-inducing molecule binding moiety is a protein or a nucleic acid binding domain or fragment of a protein, and the binding moiety is fused to a portion of the targeting moiety. The location of the targeting moiety may be either in the carboxyl-terminal or amino-terminal end of the construct or in the middle of the fusion protein.

In another embodiment, the compositions of the invention are provided as a surface component of a lipid aggregate, such as a liposome. In another embodiment, the compositions of the invention are provided encapsulated within a lipid aggregate, such as a liposome. Encapsulation may be accomplished by condensing siRNAs with cationic polymers or peptides, e.g., protamines. Liposomes, which can be unilamellar or multilamellar, can introduce encapsulated material into a cell by different mechanisms. For example, the liposome can directly introduce its encapsulated material into the cell cytoplasm by fusing with the cell membrane. Alternatively, the liposome can be compartmentalized into an acidic vacuole (i.e., an endosome) and its contents released from the liposome and out of the acidic vacuole into the cellular cytoplasm. In one embodiment the invention features a lipid aggregate formulation of the compounds described herein, including phosphatidylcholine (of varying chain length; e.g., egg yolk phosphatidylcholine), cholesterol, a cationic lipid, and 1,2-distearoyl-sn-glycero3-phosphoethanolamine-polythyleneglycol-2000 (DSPE-PEG2000). The cationic lipid component of this lipid aggregate can be any cationic lipid known in the art such as dioleoyl 1,2,-diacyl trimethylammonium-propane (DOTAP). The attached PEG can be any molecular weight but is preferably between 2000-50,000 daltons.

In one embodiment, liposomes having surface modifications, e.g., to enhance circulation time, for cryoprotection, for selective targeting, are utilized. Polyethylene glycol lipids (PEG)-modified or hyaluronic acid (HA)-coated liposomes are useful modifications for long-circulating liposomes or stealth liposomes. HA is also useful as a cryoprotectant. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011). The long-circulating compositions enhance the pharmacokinetics and pharmacodynamics of therapeutic compounds, such as DNA and RNA, particularly compared to conventional cationic liposomes which are known to accumulate in tissues of the MPS (Liu et al., J. Biol. Chem. 1995, 42, 2486424870; Choi et al., International PCT Publication No. WO 96/10391; Ansell et al., International PCT Publication No. WO 96/10390; Holland et al., International PCT Publication No. WO 96/10392). Long-circulating compositions are also likely to protect drugs from nuclease degradation to a greater extent compared to cationic liposomes, based on their ability to avoid accumulation in metabolically aggressive MPS tissues such as the liver and spleen. In another embodiment, a targeting agent may be attached to the liposome, e.g., attached to the liposome, e.g., attached to a surface modification on the liposome, e.g., HA, PEG.

The siRNAs or shRNAs of the invention, may be introduced along with components that perform one or more of the following activities: enhance uptake of the siRNA, by the cell, e.g., cervicovaginal epithelial cells, rectal epithelial cells, oral epithelial cells, genital epithelial cells, epidermal cells, neuronal cells; inhibit annealing of single strands; stabilize single strands; or otherwise facilitate delivery to the target cell and increase inhibition of the virus.

The siRNA may be directly introduced into the target cell, e.g., cervicovaginal epithelial cells, genital epithelial cells, rectal epithelial cells, genital epithelial cells, oral epithelial cells, keratinocytes, epidermal cells, neuronal cells or introduced extracellularly into a cavity, interstitial space, into the circulation of an organism, introduced orally, or may be introduced by bathing a cell or organism in a solution containing the siRNA. The siRNA may also be introduced into cells via topical application to a mucosal membrane or dermally. Vascular or extravascular circulation, the blood or lymph system, and the cerebrospinal fluid are also sites where the agents may be introduced. If necessary, biochemical components needed for RNAi to occur can also be introduced into the target cells.

A viral-mediated delivery mechanism may also be employed to deliver siRNAs to cells in vitro and in vivo as described in Xia, H. et al. (2002) *Nat Biotechnol* 20(10): 1006). Plasmid- or viral-mediated delivery mechanisms of shRNA may also be employed to deliver shRNAs to cells in vitro and in vivo as described in Rubinson, D. A., et al. ((2003) *Nat. Genet.* 33:401-406) and Stewart, S. A., et al. ((2003) *RNA* 9:493-501). Other methods of introducing siRNA molecules of the present invention to target cells include a variety of art-recognized techniques including, but not limited to, calcium phosphate or calcium chloride co-precipitation, DEAE-dextran-mediated transfection, lipofection, or electroporation as well as a number of commercially available transfection kits (e.g., OLIGOFECTAMINE® Reagent from Invitrogen) (see, e.g. Sui, G. et al. (2002) *Proc. Natl. Acad. Sci. USA* 99:5515-5520; Calegari, F. et al. (2002) *Proc. Natl. Acad. Sci., USA Oct.* 21, 2002 [electronic publication ahead of print]; J-M Jacque, K. Triques and M. Stevenson (2002) *Nature* 418:435-437; and Elbashir, S. M et al. (2001) supra). The efficiency of transfection may depend on a number of factors, including the cell type, the passage number, the confluency of the cells as well as the time and the manner of formation of siRNA- or shRNA-liposome complexes (e.g., inversion versus vortexing). These factors can be assessed and adjusted without undue experimentation by one with ordinary skill in the art.

As used herein, the term "vector" refers to a nucleic acid molecule capable of transporting another nucleic acid to which it has been linked. One type of vector is a "plasmid", which refers to a circular double stranded DNA loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors", or more simply "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, lentiviruses, adenoviruses and adeno-associated viruses), which serve equivalent functions. In a preferred embodiment, lentiviruses are used used to deliver one or more siRNA molecule of the present invention to a cell.

Within an expression vector, "operably linked" is intended to mean that the nucleotide sequence of interest is linked to the regulatory sequence(s) in a manner which allows for expression of the nucleotide sequence (e.g., in an in vitro transcription/translation system or in a target cell when the vector is introduced into the target cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). Furthermore, the siRNAs may be delivered by way of a vector comprising a regulatory sequence to direct synthesis of the siRNAs of the invention at specific intervals, or over a specific time period. It will be appreciated by those skilled in the art that the design of the expression vector can depend on such factors as the choice of the target cell, the level of expression of siRNA desired, and the like.

The expression vectors can be introduced into target cells to thereby produce siRNA molecules of the present invention. In one embodiment, a DNA template, e.g., a DNA template encoding a viral gene, such as a DNA template encoding the HSV UL5, UL27 or UL29 genes, may be ligated into an expression vector under the control of RNA polymerase III (Pol III), and delivered to a target cell. Pol III directs the synthesis of small, noncoding transcripts which 3' ends are defined by termination within a stretch of 4-5 thymidines. Accordingly, DNA templates may be used to synthesize, in vivo, both sense and antisense strands of siRNAs which effect RNAi (Sui, et al. (2002) *PNAS* 99(8):5515).

The expression vectors may also be used to introduce shRNA into target cells. The useful expression vectors also be inducible vectors, such as tetracycline (see, e.g., Wang et al. Proc Natl Acad Sci U.S.A. 100: 5103-5106, 2003) or ecdysone inducible vectors (e.g., from Invitrogen) known to one skilled in the art.

In another embodiment of the invention, the siRNA may be transported or conducted across biological membranes using carrier polymers which comprise, for example, contiguous, basic subunits, at a rate higher than the rate of transport of siRNA molecules which are not associated with carrier polymers. Combining a carrier polymer with siRNA, with or without a cationic transfection agent, results in the association of the carrier polymer and the siRNA. The carrier polymer may efficiently deliver the siRNA, across biological membranes both in vitro and in vivo. Accordingly, the invention provides methods for delivery of an siRNA, across a biological membrane, e.g., a cellular membrane including, for example, a nuclear membrane, using a carrier polymer. The invention also provides compositions comprising an siRNA in association with a carrier polymer.

The term "association" or "interaction" as used herein in reference to the association or interaction of an siRNA and a carrier polymer, refers to any association or interaction between an siRNA with a carrier polymer, e.g., a peptide carrier, either by a direct linkage or an indirect linkage. An indirect linkage includes an association between an siRNA and a carrier polymer wherein said siRNA and said carrier polymer are attached via a linker moiety, e.g., they are not directly linked. Linker moieties include, but are not limited to, e.g., nucleic acid linker molecules, e.g., biodegradable nucleic acid linker molecules. A nucleic acid linker molecule may be, for example, a dimer, trimer, tetramer, or longer nucleic acid molecule, for example an oligonucleotide of about 2, 3, 4, 5, 6, 7, 8, 9, 10, 11, 12, 13, 14, 15, 16, 17, 18, 19, 20, 21, 22, 23, 24, 25, or more nucleotides in length.

A direct linkage includes any linkage wherein a linker moiety is not required. In one embodiment, a direct linkage includes a chemical or a physical interaction wherein the two moieties, the siRNA and the carrier polymer, interact such that they are attracted to each other. Examples of direct interactions include non-covalent interactions, hydrophobic/hydrophilic, ionic (e.g., electrostatic, coulombic attraction, ion-dipole, charge-transfer), Van der Waals, or hydrogen bonding, and chemical bonding, including the formation of a covalent bond. Accordingly, in one embodiment, the siRNA and the carrier polymer are not linked via a linker, e.g., they are directly linked. In a further embodiment, the siRNA and the carrier polymer are electrostatically associated with each other.

The term "polymer" as used herein, refers to a linear chain of two or more identical or non-identical subunits joined by covalent bonds. A peptide is an example of a polymer that can be composed of identical or non-identical amino acid subunits that are joined by peptide linkages.

In one embodiment, carrier polymers in accordance with the present invention contain short-length polymers of from about 6 to up to about 25 subunits. The carrier is effective to enhance the transport rate of the siRNA across the biological membrane relative to the transport rate of the biological agent alone. Although exemplified polymer compositions are peptides, the polymers may contain non-peptide backbones and/or subunits as discussed further below.

In one aspect of the invention, the carrier polymers are particularly useful for transporting biologically active agents across cell or organelle membranes, when the siRNAs are of the type that require trans-membrane transport to exert their biological effects. As a general matter, the carrier polymer used in the methods of the invention preferably includes a linear backbone of subunits. The backbone will usually comprise heteroatoms selected from carbon, nitrogen, oxygen, sulfur, and phosphorus, with the majority of backbone chain atoms usually consisting of carbon. Each subunit may contain a sidechain moiety that includes a terminal guanidino or amidino group.

Although the spacing between adjacent sidechain moieties will usually be consistent from subunit to subunit, the polymers used in the invention can also include variable spacing between sidechain moieties along the backbone.

The sidechain moieties extend away from the backbone such that the central guanidino or amidino carbon atom (to which the $NH_2$ groups are attached) is linked to the backbone by a sidechain linker that preferably contains at least 2 linker chain atoms, more preferably from 2 to 5 chain atoms, such that the central carbon atom is the third to sixth chain atom away from the backbone. The chain atoms are preferably provided as methylene carbon atoms, although one or more other atoms such as oxygen, sulfur, or nitrogen can also be present. Preferably, the sidechain linker between the backbone and the central carbon atom of the guanidino or amidino group is 4 chain atoms long, as exemplified by an arginine side chain.

The carrier polymer sequence can be flanked by one or more non-guanidino/non-amidino subunits, or a linker such as an aminocaproic acid group, which do not significantly affect the rate of membrane transport of the corresponding polymer-containing conjugate, such as glycine, alanine, and cysteine, for example. Also, any free amino terminal group can be capped with a blocking group, such as an acetyl or benzyl group, to prevent ubiquitination in vivo.

The carrier polymer can be prepared by straightforward synthetic schemes. Furthermore, the carrier polymers are usually substantially homogeneous in length and composition, so that they provide greater consistency and reproducibility in their effects than heterogenous mixtures.

In one embodiment, the transport polymer is composed of D- or L-amino acid residues. Use of naturally occurring L-amino acid residues in the transport polymers has the advantage that break-down products should be relatively non-toxic to the cell or organism. Preferred amino acid subunits are arginine ($\alpha$-amino-$\delta$-guanidinovaleric acid) and $\alpha$-amino-$\epsilon$-amidinohexanoic acid (isosteric amidino analog). The guanidinium group in arginine has a pKa of about 12.5.

More generally, it is preferred that each polymer subunit contains a highly basic sidechain moiety which (i) has a pKa of greater than 11, more preferably 12.5 or greater, and (ii) contains, in its protonated state, at least two geminal amino groups ($NH_2$) which share a resonance-stabilized positive charge, which gives the moiety a bidentate character.

Other amino acids, such as $\alpha$-amino-$\beta$-guanidinopropionic acid, $\alpha$-amino-$\gamma$-guanidinobutyric acid, or $\alpha$-amino-$\epsilon$-guanidinocaproic acid can also be used (containing 2, 3 or 5 linker atoms, respectively, between the backbone chain and the central guanidinium carbon).

D-amino acids may also be used in the transport polymers. Compositions containing exclusively D-amino acids have the advantage of decreased enzymatic degradation. However, they may also remain largely intact within the target cell. Such stability is generally not problematic if the agent is biologically active when the polymer is still attached. For agents that are inactive in conjugate form, a linker that is cleavable at the site of action (e.g., by enzyme- or solvent-mediated cleavage within a cell) should be included to promote release of the agent in cells or organelles.

Any peptide, e.g., basic peptide, or fragment thereof, which is capable of crossing a biological membrane, either in vivo or in vitro, is included in the invention. These peptides can be synthesized by methods known to one of skill in the art. For example, several peptides have been identified which may be used as carrier peptides in the methods of the invention for transporting siRNAs across biological membranes. These peptides include, for example, the homeodomain of antennapedia, a *Drosophila* transcription factor (Wang et al., (1995) *PNAS USA.*, 92, 3318-3322); a fragment representing the hydrophobic region of the signal sequence of Kaposi fibroblast growth factor with or without NLS domain (Antopolsky et al (1999) *Bioconj. Chem.*, 10, 598-606); a signal peptide sequence of caiman crocodylus Ig(5) light chain (Chaloin et al. (1997) *Biochem. Biophys. Res. Comm.*, 243, 601-608); a fusion sequence of HIV envelope glycoprotein gp4114, (Morris et al. (1997) *Nucleic Acids Res.*, 25, 2730-2736); a transportan A-achimeric 27-mer consisting of N-terminal fragment of neuropeptide galanine and membrane interacting wasp venom peptide mastoporan (Lindgren et al., (2000), *Bioconjugate Chem.*, 11, 619-626); a peptide derived from influenza virus hemagglutinin envelop glycoprotein (Bongartz et al., 1994, *Nucleic Acids Res.*, 22, 468 1 4688); RGD peptide; and a peptide derived from the human immunodeficiency virus type-1 ("HIV-1"). Purified HIV-1 TAT protein is taken up from the surrounding medium by human cells growing in culture (A. D. Frankel and C. O. Pabo, (1988) *Cell,* 55, pp. 1189-93). TAT protein trans-activates certain HIV genes and is essential for viral replication. The full-length HIV-1 TAT protein has 86 amino acid residues. The HIV tat gene has two exons. TAT amino acids 1-72 are encoded by exon 1, and amino acids 73-86 are encoded by exon 2. The full-length TAT protein is characterized by a basic region which contains two lysines and six arginines (amino acids 47-57) and a cysteine-rich region which contains seven cysteine residues (amino acids 22-37). The basic region (i.e., amino acids 47-57) is thought to be important for nuclear localization. Ruben, S. et al., *J. Virol.* 63: 1-8 (1989); Hauber, J. et al., *J. Virol.* 63 1181-1187 (1989); Rudolph et al. (2003) 278(13):11411. The cysteine-rich region mediates the formation of metal-linked dimers in vitro (Frankel, A. D. et al., *Science* 240: 70-73 (1988); Frankel, A. D. et al., *Proc. Natl. Acad. Sci. USA* 85: 6297-6300 (1988)) and is essential for its activity as a transactivator (Garcia, J. A. et al., *EMBO J.* 7:3143 (1988); Sadaie, M. R. et al., *J. Virol.* 63: 1 (1989)). As in other regulatory proteins, the N-terminal region may be involved in protection against intracellular proteases (Bachmair, A. et al., Cell 56: 1019-1032 (1989).

In one embodiment of the invention, the basic peptide comprises amino acids 47-57 of the HIV-1 TAT peptide. In another embodiment, the basic peptide comprises amino acids 48-60 of the HIV-1 TAT peptide. In still another embodiment, the basic peptide comprises amino acids 49-57 of the HIV-1 TAT peptide. In yet another embodiment, the basic peptide comprises amino acids 49-57, 48-60, or 47-57 of the HIV-1 TAT peptide, does not comprise amino acids 22-36 of the HIV-1 TAT peptide, and does not comprise amino acids 73-86 of the HIV-1 TAT peptide. In still another embodiment, the specific peptides set forth in Table 2, below, or fragments thereof, may be used as carrier peptides in the methods and compositions of the invention.

In yet another embodiment, an active thiol at the 5' end of the sense strand may be coupled to a cysteine reside added to the C terminal end of a basic peptide for delivery into the cytosol (such as a fragment of tat or a fragment of the *Drosophila* Antennapedia peptide). Internalization via these peptides bypasses the endocytic pathway and therefore removes the danger of rapid degradation in the harsh lysosomal environment, and may reduce the concentration required for biological efficiency compared to free oligonucleotides.

Other arginine rich basic peptides are also included for use in the methods of delivery. For example, a TAT analog comprising D-amino acid- and arginine-substituted TAT(47-60), RNA-binding peptides derived from virus proteins such as HIV-1 Rev, and flock house virus coat proteins, and the DNA binding sequences of leucine zipper proteins, such as cancer-related proteins c-Fos and c-Jun and the yeast transcription factor GCN4, all of which contain several arginine residues (see Futaki, et al. (2001) J. Biol Chem 276(8):5836-5840 and Futaki, S. (2002) Int J. Pharm 245(1-2):1-7). In one embodiment, the arginine rich peptide contains about 4 to about 11 arginine residues. In another embodiment, the arginine residues are contiguous residues. In another embodiment, one of the arginine residues is substituted with D-arginine. See, for example, Melikov et al., Cell Mol Life Sci. 2005; 62: 2739-49.

Subunits other than amino acids may also be selected for use in forming transport polymers. Such subunits may include, but are not limited to hydroxy amino acids, N-methyl-amino acids amino aldehydes, and the like, which result in polymers with reduced peptide bonds. Other subunit types can be used, depending on the nature of the selected backbone.

TABLE 2

| PEPTIDE | SEQUENCE | SEQ ID NO: |
|---|---|---|
| HIV-1 TAT (49-57) | RKKRRQRRR | 31 |
| HIV-1 TAT (48-60) | GRKKRRQRRRTPQ | 32 |
| HIV-1 TAT (47-57) | YGRKKRRQRRR | 33 |
| Kaposi fibroblast growth factor | AAV ALL PAV LLA LLA P + VQR KRQ KLMP | 34 |
| of *caiman crocodylus* IG (5) light chain | MGL GLH LLV LAA ALQ GA | 35 |
| HIV envelope glycoprotein gp4 1 | GAL FLG FLG AAG STM GA + PKS IRK 5 (NLS of the SV40) | 36 |
| *Drosophila* Antennapedia | RQI KIW FQN RRM KWK K amide | 37 |
| RGD peptide | X-RGD-X | 38 |
| Influenza virus hemagglutinin envelope glycoprotein | GLFEAIAGFIENGWEGMIDGGGYC | 39 |
| transportan A | GWT LNS AGY LLG KIN LKA LAA LAK KIL | 40 |
| Pre-S-peptide | (S)DH QLN PAF | 41 |
| Somatostatin (tyr-3-octreotate) | (S)FC YWK TCT | 42 |

(s) optional Serine for coupling
bold = optional D isomer for stability

A variety of backbone types can be used to order and position the sidechain guanidino and/or amidino moieties, such as alkyl backbone moieties joined by thioethers or sulfonyl groups, hydroxy acid esters (equivalent to replacing amide linkages with ester linkages), replacing the alpha carbon with nitrogen to form an aza analog, alkyl backbone moieties joined by carbamate groups, polyethyleneimines (PEIs), and amino aldehydes, which result in polymers composed of secondary amines.

A more detailed backbone list includes N-substituted amide (CONR replaces CONH linkages), esters ($CO_2$), ketomethylene ($COCH_2$) reduced or methyleneamino ($CH_2NH$), thioamide (CSNH), phosphinate ($PO_2RCH_2$), phosphonamidate and phosphonamidate ester ($PO_2RNH$), retropeptide (NHCO), transalkene (CR=CH), fluoroalkene (CF=CH), dimethylene ($CH_22CH_2$), thioether ($CH_2S$), hydroxyethylene ($CH(OH)CH_2$), methyleneoxy ($CH_2O$), tetrazole ($CN_24$), retrothioamide (NHCS), retroreduced ($NHCH_2$), sulfonamido ($SO_2NH$), methylenesulfonamido ($CHRSO_2NH$), retrosulfonamide ($NHSO_2$), and peptoids (N-substituted glycines), and backbones with malonate and/or gem-diaminoalkyl subunits, for example, as reviewed by Fletcher et al. (1998) and detailed by references cited therein. Peptoid backbones (N-substituted glycines) can also be used. Many of the foregoing substitutions result in approximately isosteric polymer backbones relative to backbones formed from α-amino acids.

N-methyl and hydroxy-amino acids can be substituted for conventional amino acids in solid phase peptide synthesis. However, production of polymers with reduced peptide bonds requires synthesis of the dimer of amino acids containing the reduced peptide bond. Such dimers are incorporated into polymers using standard solid phase synthesis procedures. Other synthesis procedures are well known in the art.

In one embodiment of the invention, an siRNA and the carrier polymer are combined together prior to contacting a biological membrane. Combining the siRNA and the carrier polymer results in an association of the agent and the carrier. In one embodiment, the siRNA and the carrier polymer are not directly linked together. Therefore, linkers are not required for the formation of the duplex. In another embodiment, the siRNA and the carrier polymer are bound together via electrostatic bonding.

Determination of Effectiveness of Silencing

The dose of the siRNA will be in an amount necessary to effect RNA interference, e.g., post translational gene silencing (PTGS), of the particular target gene, thereby leading to inhibition of target gene expression or inhibition of activity or level of the protein encoded by the target gene. Assays to determine expression of the target sequence are known in the art. In one embodiment, a reporter gene, e.g., GFP, may be fused to the target sequence in a test cell, e.g., in a test animal. Effectiveness of silencing can then be measured by examining the reporter gene expression. Target cells which have been transfected with the siRNA molecules can be identified by routine techniques such as immunofluorescence, phase contrast microscopy and fluorescence microscopy. In one embodiment, reduced levels of target gene mRNA may be measured by in situ hybridization (Montgomery et al., (1998) *Proc. Natl. Acad. Sci., USA* 95:15502-15507) or Northern blot analysis (Ngo, et al. (1998)) *Proc. Natl. Acad. Sci., USA* 95:14687-14692). Preferably, target gene transcription is measured using quantitative real-time PCR (Gibson et al., Genome Research 6:995-1001, 1996; Heid et al., Genome Research 6:986-994, 1996). Primers for use in quantitative real-time PCR include:

```
                                        (SEQ ID NO: 15)
GAPDH-fwd           TTCACCACCATGGAGAAGGC (SEQ ID NO: 16)
GAPDH-rev           GGCATGGACTGTGGTCATGA (SEQ ID NO: 17)
TK-fwd              CGATCTACT CGCCAACACGGTG (SEQ ID NO: 18)
TK-rev              GAACGCGGAACAGGGCAAACAG (SEQ ID NO: 19)
UL5-fwd             TCGCTGGAGTCCACCTTCGAAC (SEQ ID NO: 20)
UL5-rev             CGAACTCGTGCTCCACACATCG (SEQ ID NO: 21)
UL27-fwd            CAAAGACGTGACCGTGTCGCAG (SEQ ID NO: 22)
UL27-rev            GCGGTGGTCTCCATGTTGTTCC (SEQ ID NO: 23)
UL29-fwd            GCCAGGAGATGGACGTGTTTCG (SEQ ID NO: 24)
UL29-rev            CGCGCTGTTCATCGTTCCGAAG (SEQ ID NO: 25)
STAT1-fwd           TTTGCCCAGACTCGAGCTCCTG (SEQ ID NO: 26)
STAT1-rev           GGGTGCAGGTTCGGGATTCAAC
```

-continued
```
                                        (SEQ ID NO: 27)
OAS1-fwd            GGAGGTTGCAGTGCCAACGAAG (SEQ ID NO: 28)
OAS1-rev            TGGAAGGGAGGCAGGGCATAAC (SEQ ID NO: 29)
Interferon beta-fwd CTGGAGCAGCTGAATGGAAAG (SEQ ID NO: 30)
Interferon beta-rev CTTGAAGTCCGCCCTGTAGGT
```

As used herein, "inhibition of target gene expression" includes any decrease in expression or protein activity or level of the target gene or protein encoded by the target gene as compared to a situation wherein no RNA interference has been induced. The decrease may be of at least about 30%, about 40%, about 50%, about 60%, about 70%, about 80%, about 90%, about 95% or about 99% or more as compared to the expression of a target gene or the activity or level of the protein encoded by a target gene which has not been targeted by an siRNA.

Method of Treatment and/or Prevention

The present invention provides a method for preventing viral mediated infectious disease or disorder in a subject by administering to the subject a therapeutically effective amount of one or more siRNAs as described herein. The present invention further provides a method for treating viral mediated infectious disease or disorder in a subject by administering to the subject a therapeutically effective amount of one or more siRNAs as described herein. In embodiments directed toward treatment after infection of the subject by a virus, preferably siRNAs directed to at least two viral targets are administered to the subject. The present invention still further provides a method of inhibiting expression of viral RNA, comprising administering to a subject a therapeutically effective amount of the siRNA of the present invention.

For example, the siRNAs described herein may be used as microbicides to substantially reduce transmission of diseases transmitted by viruses. Preferably, the virus is a virus described above. Preferably, the virus is an STD causing virus. Preferably, the virus is HIV, HPV, or HSV, e.g., HSV-1, HSV-2. More preferably, the virus is HSV-1 or HSV-2. Subjects at risk for an infectious disease or disorder, can be identified by, for example, any known risk factors for an infectious disease or disorder.

Another aspect of the invention pertains to methods of modulating gene expression or protein activity, e.g., cellular gene expression or activity and/or expression or activity of a gene or sequence of an infectious agent, e.g., viral gene expression or protein activity in order to treat an infectious disease or disorder. Accordingly, in an exemplary embodiment, the modulatory method of the invention involves contacting a cell with one or more siRNAs such that expression of the target gene or genes is prohibited. These methods can be performed in vitro (e.g., by culturing the cell) or, alternatively, in vivo (e.g., by administering the siRNA to a subject).

The siRNA is administered in prophylactically or therapeutically effective amounts. A prophylactically or therapeutically effective amount means that amount necessary to attain, at least partly, the desired effect, or to delay the onset of, inhibit the progression of, prevent the reoccurrence of, or halt altogether, the onset or progression of the particular condition being treated. Such amounts will depend, of course, on the particular condition being treated, the severity of the condition and individual patient parameters including age, physical condition, size, weight and concurrent treatment. These factors are well known to those of ordinary skill in the art and can be addressed with no more than routine experimentation. It is preferred generally that a maximum dose be used, that is, the highest safe dose according to sound medical judgment. It will be understood by those of ordinary skill in the art; however, that a lower dose or tolerable dose may be administered for medical reasons, psychological reasons or for virtually any other reason.

The term "therapeutically effective amount" refers to an amount that is sufficient to effect a therapeutically or prophylactically significant reduction in production of infectious virus particles and reduction in viral shedding when administered to a typical subject who is infected with a virus and at risk of transmitting the virus, including through sexual contact and childbirth, or who is infected with a virus and is at risk of reactivation of a viral infection, or who is infected with a virus and is at risk of reinfection with a virus or who is at risk of being infected with a virus. A therapeutically or prophylactically significant reduction is about 30%, about 40%, about 50%, about 60%, about 70%, about 80%, about 90%, about 100%, about 125%, about 150% or more compared to a control.

The term "preventing" as used herein refers to preventing viral infection in an individual susceptible for infection or re-infection. Accordingly, administration of a prophylactic agent can occur prior to the manifestation of symptoms characteristic of an infectious disease or disorder, such that the infectious disease or disorder is prevented or, alternatively, delayed in its progression. Any mode of administration of the therapeutic agents of the invention, as described herein or as known in the art, including topical administration or mucosal administration of the siRNAs of the instant invention, may be utilized for the prophylactic treatment of an infectious disease or disorder.

Whether effective prevention is achieved can be tested using routine viral infection detection methods including, but not limited to by microscopic examination of lesion samples, or biopsies from e.g. skin, brain or liver for multinucleate giant cells with eosinophilic intranuclear inclusion bodies, or by various immunofluorescence techniques (e.g., ELISA), by FDA approved tests based on immunological techniques including but not limited to biokitHSV-2 Rapid Test (biokit USA), HERPESELECT® Elisa and HERPESELECT® Immunoblot (diagnostic kits for the type-specific detection of HSV 1 and 2; Focus Diagnostics, Inc.), and CAPTIA™ HSV IgG Type Specific ELISA (Trinity Biotech USA), or by herpes western blot (University of Washington), or by quantitative PCR monitoring viral load. For example, to test effectiveness of a specific siRNA or dosage, a mouse model can be used. Viral shedding from the genital epithelium can be determined by swabbing (Micropur swab, PurFybr Inc) the vaginal cavity and titrating virus on Vero cells.

Formulations of the siRNA as described herein may be administered to a subject at risk for an virus-mediated disease or disorder, e.g., a viral disorder, such as HSV-1 or HSV-2, or another sexually transmitted disease or infection, or any other infectious agent, e.g., a virus, as a topically applied prophylactic, e.g., for administration on mucosal membranes, e.g., orally, genitally, cervicovaginally, or rectally, or topically to epithelia or epiderma, to prevent transmission of a viral or bacterial disease or disorder, such as HSV-1 or HSV-2, or another sexually transmitted disease or infection. In one embodiment, the compositions comprising the siRNA and the carrier polymer may be administered prior to exposure to the infectious agent. In vitro experiments illustrate that the antiviral state induced by introduced duplex siRNAs can last for weeks. Therefore, in one embodiment, an siRNA-based microbicide need not be applied before each sexual encounter. Accordingly, in another embodiment, the prophylactic effect of the siRNA is prolonged, e.g., lasts for at least one week, preferably two or more weeks. In another embodiment, the compositions comprising the siRNA may be administered, e.g., topically, at intervals, e.g., one or more times per week, or one or more times per month, rather than directly prior to exposure to an infectious agent. In one embodiment, the siRNA is administered to neuronal cells, e.g., cells of the sacral ganglia or trigeminal ganglia, to treat a latent infection or prevent reactivation of a latent infection, e.g., a latent infection of HSV.

For example, the therapeutic agents described herein may be formulated as a spray, lotion, cream, foam, gel, and the like, or any other suitable delivery method known in the art or described herein, and may include, for example, standard lubricants and/or detergents or other additives. In one embodiment, these formulations are administered in combination with barrier methods for protection against sexually transmitted diseases, or may be applied to condoms or other barrier protection devices.

The topically applied agents may also be used in combination with a spermicidal or other microbicidal agent as described in, for example, U.S. Pat. No. 6,302,108, the entire contents of which are expressly incorporated herein, or in combination with other prophylactic agents for the prevention of HIV or other STDs. The compounds can also be prepared in the form of suppositories for cervicovaginal or rectal delivery, e.g., with conventional suppository bases such as cocoa butter and other glycerides, or retention enemas for rectal delivery.

The prophylactic or therapeutic pharmaceutical compositions of the invention can contain other pharmaceuticals, in conjunction with a vector according to the invention, when used to therapeutically treat viral mediated disease, such as disease mediated by a virus described above, and can also be administered in combination with other pharmaceuticals used to treat viral mediated disease, such as with conventional antiviral therapy. For example, the prophylactic or therapeutic pharmaceutical compositions of the invention can also be used in combination with other pharmaceuticals which treat or alleviate symptoms of viral infection such as acyclovir, valacyclovir, famciclovir, penciclovir, vidarabine, ganciclovir, idoxuridine, foscarnet, trifluridine, levamisole, amlexanox, lidocaine, docosanol, tetracaine, diphenhydramine, hydroxyzine, aspirin or aspirin derivative, lysine or any combination thereof.

Pharmaceutical Compositions

The siRNA of the invention can be incorporated into pharmaceutical or microbicidal compositions suitable for administration. Such compositions typically comprise the siRNA targeting a viral gene, and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Generally, the compositions of the instant invention are introduced by any standard means, with or without stabilizers, buffers, and the like, to form a pharmaceutical composition. For use of a liposome delivery mechanism, standard protocols for formation of liposomes can be followed. The compositions of the present invention can also be formulated and used as tablets, capsules or elixirs for oral administration; suppositories for vaginal or rectal administration; sterile solutions; suspensions for injectable administration; and the like.

Examples of routes of administration include parenteral, e.g., intravenous, intramuscular, intradermal, subcutaneous, oral (e.g., inhalation), transdermal (topical), transmucosal, genital, vaginal, cervicovaginal and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. The compounds can also be prepared in the form of suppositories (e.g., with conventional suppository bases such as cocoa butter and other glycerides) or retention enemas for rectal delivery.

Systemic administration can also be topical, e.g., by transmucosal or transdermal means. Suitable formulations for topical, particularly vaginal or rectal, administration include solutions, suspensions, gels, lotions and creams as well as discrete units such as suppositories and microencapsulated suspensions. For transmucosal or transdermal administration, penetrants appropriate to the barrier to be permeated are used in the formulation. Such penetrants are generally known in the art, and include, for example, for transmucosal administration, detergents, bile salts, and filsidic acid derivatives. Transmucosal administration can be accomplished through the use of nasal sprays, suppositories or the formulations of the transdermal administrations. For transdermal administration, the active compounds are formulated into ointments, salves, gels, or creams as generally known in the art. Transmucosal drug delivery in the form of a polytetrafluoroethylene support matrix is described in U.S. Pat. No. 5,780,045 (specifically incorporated herein by reference in its entirety).

Delivery systems can include sustained release delivery systems which can provide for slow release of the active component of the invention, including sustained release gels, creams, suppositories, or capsules. In one embodiment, the active compounds are prepared with carriers that will protect the compound against rapid elimination from the body, such as a controlled release formulation, including implants and microencapsulated delivery systems. Sustained release delivery systems include, but are not limited to: (a) erosional systems in which the active component is contained within a matrix, and (b) diffusional systems in which the active component permeates at a controlled rate through a polymerBiodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to hepatocytes) can also be used as pharmaceutically acceptable carriers. These can be prepared according to methods known to those skilled in the art, for example, as described in U.S. Pat. No. 4,522,811 and U.S. Pat. No. 5,643,599, the entire contents of which are incorporated herein.

The pharmaceutical compositions of the present invention can be utilized in conjunction with a delivery device, e.g., microbicidal delivery device, by applying the agents on the device or as a component of the device, including for example, a condom, a contraceptive diaphragm, a cervical cap, a vaginal ring (e.g., NUVARING® etonogestrel/ethinyl estradiol vaginal ring), cellulose sulfate gel (UsherCell, Polydex Pharmaceuticals Ltd., Nassau Bahamas) or a contraceptive sponge, such as, a collagen sponge or a polyurethane foam sponge (TODAY SPONGE®). Alternatively, the delivery device is not also a contraceptive device. Alternatively, the pharmaceutical composition of the present invention can be applied on a pessary, tampon or suppository.

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described e.g., in U.S. Pat. No. 5,756,353 and U.S. Pat. No. 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts.

In another embodiment, pharmaceutical compositions may be delivered by ocularly via eyedrops.

Liposomal suspensions (including liposomes targeted to macrophages containing, for example, phosphatidylserine) can also be used as pharmaceutically acceptable carriers. These can be prepared according to methods known to those skilled in the art, for example, as described in U.S. Pat. No. 4,522,811 U.S. Pat. No. 5,643,599, the entire contents of which are incorporated herein. Alternatively, the therapeutic agents of the invention may be prepared by adding a poly-G tail to one or more ends of the siRNA for uptake into target cells.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fingi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the siRNA in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yield a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of an siRNA (i.e., an effective dosage) ranges from about 0.001 to 3000 mg/kg body weight, preferably about 0.01 to 2500 mg/kg body weight, more preferably about 0.1 to 2000 mg/kg body weight, and even more preferably about 1 to 1000 mg/kg, 2 to 900 mg/kg, 3 to 800 mg/kg, 4 to 700 mg/kg, or 5 to 600 mg/kg body weight. In one embodiment, the average adult is 60 kg and is administered about 0.5 to 50 mg, about 1 to 45 mg, about 2 to 40, about 3 to 35 mg, about 4 to 30 mg, about 5 to 25 mg, about 6 to 20 mg of siRNA. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an siRNA can include a single treatment or, preferably, can include a series of treatments.

Generally, at intervals to be determined by the prophylaxis or treatment of pathogenic states, intra-genital or intra-mucosal doses of active component will be from about 0.01 mg/kg per day to 1000 mg/kg per day. Small doses (0.01-1 mg) may be administered initially, followed by increasing doses up to about 1000 mg/kg per day. In the event that the response in a subject is insufficient at such doses, even higher doses (or effective higher doses by a different, more localized delivery route) may be employed to the extent patient tolerance permits. Multiple doses per day can be contemplated to achieve appropriate systemic levels of compounds.

It is understood that appropriate doses of the siRNAs depend upon a number of factors within the ken of the ordinarily skilled physician, veterinarian, or researcher. The dose(s) of the agent will vary, for example, depending upon the identity, size, and condition of the subject or sample being treated, further depending upon the route by which the composition is to be administered, if applicable, and the effect which the practitioner desires the siRNA to have upon the virus.

The pharmaceutical compositions can be included in a container, pack, or dispenser together with instructions for administration.

This invention is further illustrated by the following examples which should not be construed as limiting.

EXAMPLE

Methods
Mice.
BALB/c mice (5-8 weeks old) were from Taconic Farms; FVB.Cg-Tg (GFPU)5Nagy mice were from Jackson Laboratories (11). Mice subcutaneously injected with 2 mg medroxyprogesterone acetate (Sicor) 1 wk earlier were infected with $10^4$ (~2 LD50) HSV-2 strain 186 per vagina (21). siRNA (500 pmole) complexed with Oligofectamine (Invitrogen), prepared according to the manufacturer's protocol, was administered per vagina in a maximal volume of 12 ul in two regimens—2 hr before and 4 hr after HSV-2 infection or 1 and 2 hr after HSV-2 infection. Mice were examined daily for signs of HSV-2 graded by a 5-point scale (0, no signs of infection; 1, slight genital erythema and edema; 2, moderate genital inflammation; 3, purulent genital lesions; 4, hind limb paralysis; 5, death) (21). Viral shedding from the genital epithelium was determined by swabbing (Micropur swab, PurFybr Inc) the vaginal cavity on day 6 post-infection and titrating virus on Vero cells. In some cases, the vagina was dissected at indicated times and either fixed in 10% formalin (Sigma) for paraffin embedding and sectioning, or stored in RNAlater (Qiagen) for RNA isolation.

Viruses and Transfection Assays.

For in vitro studies, 186ΔKpn, a replication-competent, thymidine kinase-negative mutant of strain 186syn+22 was grown in Vero cells as described (23). Vero or NIH3T3 cells (ATCC) ($4 \times 10^5$ cells/well in 6 well plates in 1 ml of complete medium, plated 1 day earlier), were treated with 100 μmol siRNA, complexed with TransIT-TKO (Mirus) to transfect Vero cells or with TransIT-siQuest (Mirus) for NIH3T3 cells according to the manufacturer's instructions. After overnight incubation at 37 C, medium was replaced, and 2 hrs later HSV-2 186ΔKpn was added at an MOI=1. After 1 hr at 37 C, medium was again replaced. Cells were harvested 24 hr later and viral titer determined by plaque assay on Vero cells. For mouse experiments wild-type HSV-2 strain 186syn+virus was used (24). An aliquot of virus used for each mouse experiment was also assayed by plaque assay to confirm viral titer.

siRNAs.

siRNAs (Dharmacon) were prepared according to manufacturer's instructions. FITC-labeled siRNA was a previously described sequence targeting CD425. The sequence for silencing EGFP was described (25). The sequences for HSV-2 (Genbank accession no. NC 001798) were

```
UL5.1 (nt 12838-12856)
                                        (SEQ ID NO: 1)
sense:          5'-CUA CGG CAU CAG CUC CAA A-3'

(SEQ ID NO: 2)
antisense:      5'-UUU GGA GCU GAU GCC GUA G-3'

UL5.2 (nt 12604-12622)
                                        (SEQ ID NO: 3)
sense:          5'-UGU GGU CAU UGU CUA UUA A-3'

(SEQ ID NO: 4)
antisense:      5'-UUA AUA GAC AAU GAC CAC A-3'

UL27.1 (nt 54588-54606)
                                        (SEQ ID NO: 5)
sense:          5'-GUU UAC GUA UAA CCA CAU A-3'

(SEQ ID NO: 6)
antisense:      5'-UAU GUG GUU AUA CGU AAA C-3'

UL27.2 (nt 54370-54388)
                                        (SEQ ID NO: 7)
sense:          5'-ACG UGA UCG UGC AGA ACU C-3'

(SEQ ID NO: 8)
antisense:      5'-GAG UUC UGC ACG AUC ACG U-3'

UL27.3 (nt 54097-54115)
                                        (SEQ ID NO: 9)
sense:          5'-UCG ACC UGA ACA UCA CCA U-3'

(SEQ ID NO: 10)
antisense:      5'-AUG GUG AUG UUC AGG UCG A-3'

UL29.1 (nt 60324-60342)
                                        (SEQ ID NO: 11)
sense:          5'-CUU UCG CAA UCA AUU CCA A-3'

(SEQ ID NO: 12)
antisense:      5'-UUG GAA UUG AUU GCG AAA G-3'

UL29.2 (nt 59715-59733)
                                        (SEQ ID NO: 13)
sense:          5'-CCA CUC GAC GUA CUU CAU A-3'

(SEQ ID NO: 14)
antisense:      5'-UAU GAA GUA CGU CGA GUG G-3'
```

Quantitative RT-PCR.

Total RNA, extracted and stored in RNAlater (Qiagen), was isolated using the RNeasy RNA isolation kit (Qiagen) according to the manufacturer's protocol. Total RNA (1 ug) was reverse transcribed using Superscript III (Invitrogen) and random hexamers, according to the manufacturer's protocol. Real-time PCR was performed on 0.2 ul of cDNA, or a comparable amount of RNA with no reverse transcriptase, using Platinum Taq Polymerase (Invitrogen) and a Biorad iCycler. SYBR green (Molecular Probes, Oregon) was used to detect PCR products. Reactions were performed in a 25 ul reaction volume in triplicate. Primers used are:

```
                                        (SEQ ID NO: 15)
GAPDH-fwd           5'-TTCACCACCATGGAGAAGGC-3', (SEQ ID NO: 16)
GAPDH-rev           5'-GGCATGGACTGTGGTCATGA-3', (SEQ ID NO: 17)
TK-fwd              5'-CGATCTACT CGCCAACACGGT G-3'

(SEQ ID NO: 18)
TK-rev              5'-GAACGCGGAACAGGGCAAACAG-3'

(SEQ ID NO: 19)
UL5-fwd             5'-TCGCTGGAGTCCACCTTCGAAC-3'

(SEQ ID NO: 20)
UL5-rev             5'-CGAACTCGTGCTCCACACATCG-3'

(SEQ ID NO: 21)
UL27-fwd            5'-CAAAGACGTGACCGTGTCGCAG-3'

(SEQ ID NO: 22)
UL27-rev            5'-GCGGTGGTCTCCATGTTGTTCC-3'

(SEQ ID NO: 23)
UL29-fwd            5'-GCCAGGAGATGGACGTGTTTCG-3'

(SEQ ID NO: 24)
UL29-rev            5'-CGCGCTGTTCATCGTTCCGAAG-3'

(SEQ ID NO: 25)
STAT1-fwd           5'-TTTGCCCAGACTCGAGCTCCTG-3'

(SEQ ID NO: 26)
STAT1-rev           5'-GGGTGCAGGTTCGGGATTCAAC-3'

(SEQ ID NO: 27)
OAS1-fwd            5'-GGAGGTTGCAGTGCCAACGAAG-3'

(SEQ ID NO: 28)
OAS1-rev            5'-TGGAAGGGAGGCAGGGCATAAC-3'

(SEQ ID NO: 29)
Interferon beta-fwd 5'-CTGGAGCAGCTGAATGGAAAG-3'

(SEQ ID NO: 30)
Interferon beta-rev 5'-CTTGAAGTCCGCCCTGTAGGT-3'
```

PCR parameters consisted of 5 min of Taq activation at 95 C, followed by 40 cycles of PCR at 95 C×20 sec, 60 C×30 sec, and 69 C×20 sec. Standard curves were generated and the relative amount of target gene mRNA was normalized to GAPDH mRNA. Specificity was verified by melt curve analysis and agarose gel electrophoresis.

Tissue Sections and Microscopy.

For analysis of fluorescent tissue, dissected tissue was placed in Oct compound (TissueTek) and snap frozen in LN2. For hematoxylin-eosin stained sections, tissues were fixed in 10% formalin and paraffin-embedded. Microscopy was performed on a Zeiss Axiovert 200M microscope using Slidebook acquisition and analysis software (Intelligent Imaging).

Statistical Analysis.

In vitro experimental data was analyzed by student's t-test. Survival distribution was calculated using the Kaplan and Meier method (26), and the univariate comparison of survival distributions for treated vs. control groups was tested using the log-rank test, comparing 2 groups at a time (27). The approach of generalized estimating equations was used to model the disease scores collected over time and to compare disease severity of treated vs. control groups (28). All p-values reported are for two-sided significance tests.

Results

To determine whether siRNAs are taken up into the genital mucosa, we instilled FITC-siRNA complexed with Oligofectamine into the mouse vagina. Fluorescence was observed 24 hr later in cells throughout the vaginal and ectocervical mucosa and the underlying lamina propria (FIG. 1a). To determine whether these siRNAs effectively silence gene expression in the vagina, siRNAs targeting EGFP and inverted control siRNAs were administered intravaginally with Oligofectamine to GFP mice that express EGFP in every cell from the beta-actin promoter (11). Three days later, GFP expression was down-modulated in GFP siRNA-treated mice, but not in control mice (FIG. 1b). Silencing was also evident throughout the cervix, but there was no systemic silencing in distant organs like the liver. Because silencing can persist for several weeks in cells that are not dividing, we looked at the durability of silencing. Silencing lasted without diminution for at least 9 days (as long as the experiments were conducted) under conditions where epithelial turnover was reduced by treatment with medroxyprogesterone acetate (FIG. 1c). The extent and persistence of local silencing demonstrates that siRNAs are active in a microbicide. Moreover the durability of silencing suggests that an RNAi-mediated microbicide might not need to be administered just prior to sexual intercourse, mitigating one of the major problems with microbicides, compliance.

Figure 2:
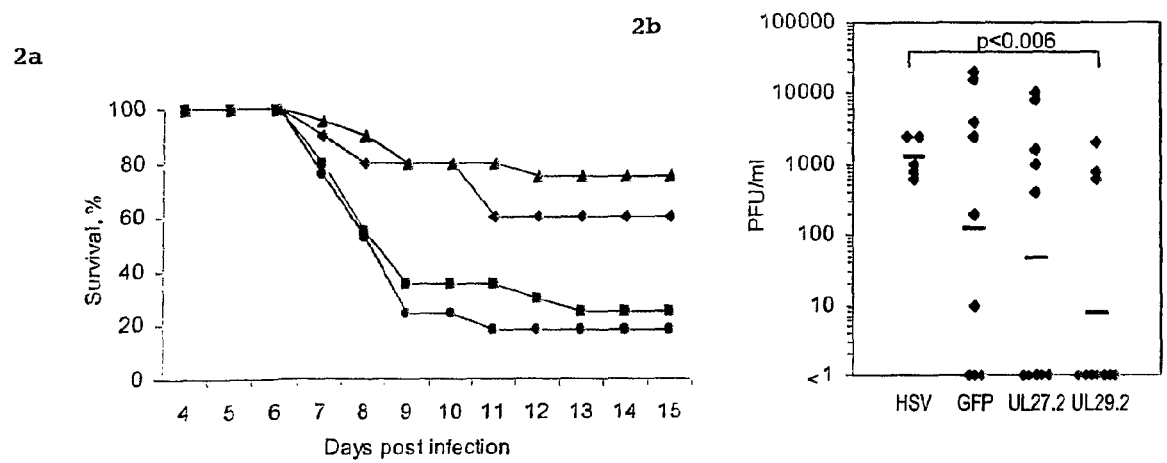

To determine whether the profound silencing observed for an endogenous gene could be harnessed to protect against sexually transmitted infection, we designed 7 siRNAs targeting 3 essential HSV-2 genes—UL5, encoding a component of the helicase-primase complex; UL27, which encodes the envelope glycoprotein B; and UL29, encoding a DNA-binding protein (5). siRNAs were chosen using the Dharmacon design program, which included a criterion that would favor unwinding from the 5'-end of the antisense strand (12-14). After overnight transfection with lipid-complexed siRNAs targeting HSV-2 or control EGFP, NIH3T3 (FIG. 2a) and Vero (FIG. 2b) cells were infected with HSV-2 186 at a multiplicity of infection (MOI) of 1, and viral replication was assessed by plaque assay 24 hr later. Three of the siRNAs (UL5.2, UL27.2 and UL29.2) resulted in significant decreases in viral titer, with reductions ranging from 5 to 62 fold. Transfection of the GFP siRNA did not reproducibly decrease viral titer. UL29.2 was the most effective siRNA at suppressing viral production in both cell lines, suppressing viral replication by 25-fold in Vero cells and 62-fold in NIH3T3 cells. The effectiveness of silencing was also analyzed by quantitative RT-PCR amplification of viral mRNAs that encode the viral thymidine kinase TK as well as the targeted UL5, UL27 and UL29 genes (FIG. 2c). RNA was isolated from Vero cells harvested 24 hr after HSV-2 infection at an MOI of 1 and was normalized to GAPDH expression. Transfection with control siRNA targeting EGFP had no significant effect on viral gene transcription. Silencing of viral gene expression roughly paralleled inhibition of viral replication with UL29.2 siRNA proving to be the most effective, suppressing relative viral gene expression by 4-5 fold. UL5.2 and UL27.2 siRNAs each inhibited viral gene expression by about 3-fold. Silencing any of the 3 viral genes effectively silenced the expression of the other nontargeted viral genes, demonstrating the importance of each of these genes for viral replication and spread.

Figure 3:
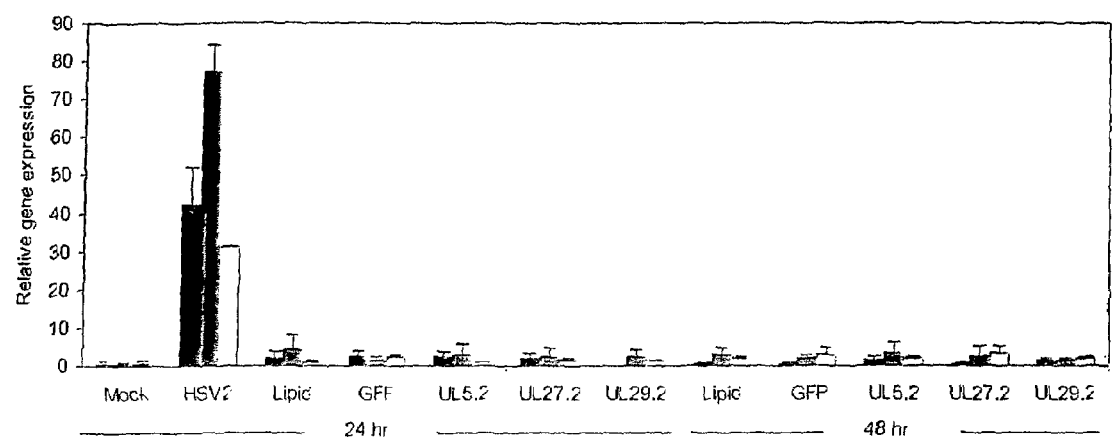
FIG. 3 shows topical lipid-complexed siRNAs do not activate inflammation or IRGs. Vaginal tissue, dissected 24 and 48 hr after administering 500 pmole of lipid-complexed siRNA, was assessed for relative expression of IFN-beta (black) and the IRGs STAT1 (gray) and OAS1 (white) compared to GAPDH by quantitative RT-PCR. HSV-2 infection was used as a positive control for IFN induction. There was no significant change in gene expression compared to mock-treated mice by any of the siRNAs.

We next investigated whether treatment with siRNAs targeting HSV-2 could protect mice from vaginal infection. Because UL29.2 was the most effective siRNA, in initial experiments groups of 5-10 mice were treated per vagina with 0.5 nmol of UL29.2 siRNA or control GFP siRNA delivered with Oligofectamine 2 hrs prior and 4 hrs following infection with 2 LD50 ($10^4$ pfu) of HSV-2 wild-type virus. The mice were pretreated with medroxyprogesterone acetate 1 week earlier to reduce variations in infectivity due to differences in menstrual cycle. Treatment with UL29.2 siRNA provided highly significant protection, assessed daily by a clinical disease scoring system or by survival (FIG. 3a, b). While 75% of infected mice treated with GFP siRNA (15/20) or no siRNA (13/17) died, only 25% of mice treated with UL29.2 siRNA (5/20) died (time to death comparison by log rank test, p<0.001 vs no treatment, p<0.003 vs GFP siRNA). Although 60% of mice treated with UL29.2 siRNA developed some signs of infection from this lethal challenge, the surviving mice had no clinical symptoms of disease by day 11. A longitudinal regression analysis of disease severity over time and between groups showed robust protection in UL29.2 siRNA-treated mice (p<0.001 vs no treatment, p<0.006 vs GFP siRNA control mice when analyzed with respect to time course; p<0.001 vs either control group when analyzed between groups). Mice treated with UL27.2 siRNA, which was less effective in vitro, were also partially protected by disease score and survival, but protection was less effective. Sixty percent (6/10) of mice survived the lethal vaginal challenge (p<0.009 compared to untreated, p=0.10 compared to GFP siRNA-treated mice). Moreover, protection from disease severity in UL27.2 siRNA-treated mice analyzed by longitudinal regression analysis was highly significant (p<0.001 compared to untreated, p<0.006 compared to GFP siRNA-treated mice with respect to time; p<0.01 and p=0.05, analyzed between the respective groups). When siRNA treatment was deferred until after vaginal challenge in 1 pilot experiment involving 5 mice per group, there was a trend towards a survival advantage in mice treated 1 and 2 hr after infection with UL29.2. While 3 mice in the UL29.2 group and 2 mice in the UL27.2 group survived, none survived of the mice not given siRNAs and 1 mouse survived in the group given GFP siRNA (p=0.08 for UL29.2, ns for UL27.2 by log-rank test). Further experiments to optimize post-exposure therapy are in progress.

The clinical advantage afforded by treatment with antiviral siRNAs was also evident by quantifying genitally shed virus obtained by vaginal swab 6 days following infection (FIG. 3c). While all infected mice that were not given siRNAs shed virus on day 6, no virus was detected in 70% of UL29.2- and 50% of UL27.2-treated mice. No virus was isolated from 3 of 9 control GFP siRNA-treated mice, but this was not significantly different from untreated mice. The geometric mean viral titer was reduced by more than 2 logs by UL29.2 treatment from 1226 pfu/ml in untreated mice to 7.9 pfu/ml in mice that received UL29.2 (p<0.006). Viral shedding at day 6 predicted survival since 18 of 19 mice that had detectable plaques died, while none of the 15 mice with undetectable virus died. Analysis of cervicovaginal histology by hematoxylin-eosin staining of mice sacrificed at day 6 also showed substantial preservation of vaginal mucosa by treatment with antiviral siRNAs (FIG. 3d). In the control, infected mice that were pretreated either with no siRNA or GFP siRNA, the mucosal epithelium was partially denuded, and apoptosis and inflammatory infiltrates were prominent. Multinucleated cells with intranuclear inclusion bodies, a hallmark of HSV-2 infection, were also evident. By contrast, the epithelium was intact and there were few apoptotic bodies and scarcely any inflammatory cells in UL27.2 or UL29.2 siRNA-treated mice.

Some recent studies suggest that under certain circumstances siRNA treatment can induce the interferon pathway and initiate inflammatory responses (15-18). To rule out the possibility that the treatment was toxic or that antiviral protection was due to non-specific effects, we analyzed vaginal tissue, obtained 24 and 48 hr after treatment of uninfected mice with lipid-complexed control or antiviral siRNAs, for inflammatory infiltrates by hematoxylin-eosin staining (FIG. 4a) and for induction of interferon and interferon responsive genes (IRG) (FIG. 4b). siRNA treatment does not cause an inflammatory infiltrate. Moreover, RNA isolated at the expected peak time for induction of interferon and IRG (1 and 2 days) did not show a significant induction of expression of IFN-beta or the key IRGs, OAS1 or STAT1, by quantitative RT-PCR when compared to mock-treated mice. As expected, HSV2 infection, used as a positive control, in the absence of siRNAs activated IRGs.

The contents of all references, patents and published patent applications cited throughout this application are incorporated herein by reference in their entirety.

REFERENCES

1. Whitley, R. J. in Fields Virology (eds. Knipe, D. M. & Howley, P. M.) 2461-2510 (Lippincott Williams and Wilkins, Philadelphia, 2001).
2. Wald, A. & Link, K. Risk of human immunodeficiency virus infection in herpes simplex virus type 2-seropositive persons: a meta-analysis. J Infect Dis 185, 45-52 (2002).
3. Celum, C., Levine, R., Weaver, M. & Wald, A. Genital herpes and human immunodeficiency virus: double trouble. Bull World Health Organ 82, 447-453 (2004).
4. Pilcher, H. Starting to gel. Nature 430, 138-140 (2004).
5. Roizman, B. & Knipe, D. M. in Fields Virology (eds. Knipe, D. M. & Howley, P. M.) 2399-2440 (Lippincott Williams & Wilkins, Philadelphia, 2001).
6. Shankar, P., Manjunath, N. & Lieberman, J. The prospect of silencing disease using RNA interference. JAMA 293, 1367-1373 (2005).
7. Ge, Q. et al. Inhibition of influenza virus production in virus-infected mice by RNA interference. Proc Natl Acad Sci USA 101, 8676-8681 (2004).
8. Tompkins, S. M., Lo, C. Y., Tumpey, T. M. & Epstein, S. L. Protection against lethal influenza virus challenge by RNA interference in vivo. Proc Natl Acad Sci USA 101, 8682-8686 (2004).
9. Bitko, V., Musiyenko, A., Shulyayeva, O. & Barik, S. Inhibition of respiratory viruses by nasally administered siRNA. Nat Med 11, 50-55 (2005).
10. Zhang, W. et al. Inhibition of respiratory syncytial virus infection with intranasal siRNA nanoparticles targeting the viral NS1 gene. Nat Med 11, 56-62 (2005).
11. Hadjantonakis, A. K., Gertsenstein, M., Ikawa, M., Okabe, M. & Nagy, A. Generating green fluorescent mice by germline transmission of green fluorescent ES cells. Mech Dev 76, 79-90 (1998).
12. Khvorova, A., Reynolds, A. & Jayasena, S. D. Functional siRNAs and miRNAs exhibit strand bias. Cell 115, 209-216 (2003).
13. Schwarz, D. S. et al. Asymmetry in the assembly of the RNAi enzyme complex. Cell 115, 199-208 (2003).
14. Reynolds, A. et al. Rational siRNA design for RNA interference. Nat Biotechnol 22, 326-330 (2004).
15. Sledz, C. A., Holko, M., de Veer, M. J., Silverman, R. H. & Williams, B. R. Activation of the interferon system by short-interfering RNAs. Nat Cell Biol 5, 834-839 (2003).
16. Heidel, J. D., Hu, S., Liu, X. F., Triche, T. J. & Davis, M. E. Lack of interferon response in animals to naked siRNAs. Nat Biotechnol 22, 1579-1582 (2004).
17. Hornung, V. et al. Sequence-specific potent induction of IFN-alpha by short interfering RNA in plasmacytoid dendritic cells through TLR7. Nat Med 11, 263-270 (2005).
18. Judge, A. D. et al. Sequence-dependent stimulation of the mammalian innate immune response by synthetic siRNA. Nat Biotechnol 23, 457-462 (2005).
19. Manoharan, M. RNA interference and chemically modified small interfering RNAs. Curr Opin Chem Biol 8, 570-579 (2004).
20. Lee, S. K. et al. Lentiviral delivery of short hairpin RNAs protects CD4 T cells from multiple clades and primary isolates of HIV. Blood (2005).
21. Morrison, L. A., Da Costa, X. J. & Knipe, D. M. Influence of mucosal and parenteral immunization with a replication-defective mutant of HSV-2 on immune responses and protection from genital challenge. Virology 243, 178-187 (1998).
22. Jones, C. A., Taylor, T. J. & Knipe, D. M. Biological properties of herpes simplex virus 2 replication-defective mutant strains in a murine nasal infection model. Virology 278, 137-150 (2000).
23. Gao, M. & Knipe, D. M. Genetic evidence for multiple nuclear functions of the herpes simplex virus ICP8 DNA-binding protein. J Virol 63, 5258-5267 (1989).
24. Spang, A. E., Godowski, P. J. & Knipe, D. M. Characterization of herpes simplex virus 2 temperature-sensitive mutants whose lesions map in or near the coding sequences for the major DNA-binding protein. J Virol 45, 332-342 (1983).
25. Novina, C. D. et al. siRNA-directed inhibition of HIV-1 infection. Nat Med 8, 681-686. (2002).
26. Kaplan, E. L. & Meier, R. Non-parametric estimation from incomplete observation. J Am Stat Assoc 53, 457-581 (1958).
27. Mantel, N. Evaluation of survival data and two new rank order statistics arising in its consideration. Cancer Chemother Rep 50, 163-170 (1966).
28. Zeger, S. L. & Liang, K. Y. Longitudinal data analysis for discrete and continuous outcomes. Biometrics 42, 121-130 (1986).

The invention claimed is:

1. A method of treating or preventing HSV-2 infection, comprising administering to a cell an effective amount of a microbicide comprising at least one siRNA, comprising a pharmaceutically acceptable carrier and the siRNA, wherein the siRNA comprises an RNA duplex comprised of one or two molecules, wherein a portion of the molecule comprises a nucleotide sequence selected from SEQ ID NO: 13 and SEQ ID NO: 14 or a combination thereof.

2. The method of claim 1, wherein the cell is a human cell.

3. The method of claim 2, wherein the cell is located in a human subject.

4. The method of claim 3, wherein the cell is located in the genitalia, cervicovagina, rectum, oral cavity, lips, mouth, skin, or eyes of the subject.

5. The method of claim 1, wherein the pharmaceutically acceptable carrier further comprises a liposome.

6. The method of claim 1, wherein the pharmaceutically acceptable carrier further comprises a condensation agent.

7. The method of claim 6, wherein the condensation agent is a protamine.

8. The method of claim 1, wherein the pharmaceutically acceptable carrier further comprises a targeting agent.

9. The method of claim 1, wherein the at least one siRNA is expressed from an vector.

10. The method of claim 1, wherein the microbicide is administered by a topical administration.

11. The method of claim 10, wherein the topical composition is administration is cervicovaginal.

12. The method of claim 1, wherein the microbicide is associated with a physical vehicle.

13. The method of claim 12, wherein the physical vehicle is a contraceptive device.

14. The method of claim 12, wherein the physical vehicle is selected from the group consisting of a polyurethane foam, a cellulose sulfate gel or a suppository.

15. The method of claim 1, wherein the microbicide is administered by enteral administration.

16. The method of claim 1, wherein the microbicide is administered by a parenteral administration.

17. The method of claim 1, wherein the microbicide is administered in combination with a pharmaceutical agent for treating the viral disease, wherein the pharmaceutical agent is different from the siRNA and is selected from the group consisting of acyclovir, valacyclovir, famciclovir, penciclovir, vidarabine, ganciclovir, idoxuridine, foscarnet, trifluridine, levamisole, amlexanox, lidocaine, docosanol, tetracaine, diphenhydramine, hydroxyzine, aspirin or aspirin derivative, lysine or any combination thereof.

* * * * *

SEQUENCE LISTING

<160> NUMBER OF SEQ ID NOS: 50

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA

<400> SEQUENCE: 1
cuacggcauc agcuccaaa                                                   19

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA

<400> SEQUENCE: 2
uuuggagcug augccguag                                                   19

<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA

<400> SEQUENCE: 3
uguggucauu gucuauuaa                                                   19

<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA

<400> SEQUENCE: 4
uuaauagaca augaccaca                                                   19

<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA

<400> SEQUENCE: 5
guuuacguau aaccacaua                                                   19

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA

<400> SEQUENCE: 6

```
uaugugguua uacguaaac                                               19

<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA

<400> SEQUENCE: 7
acgugaucgu gcagaacuc                                               19

<210> SEQ ID NO 8
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA

<400> SEQUENCE: 8
gaguucugca cgaucacgu                                               19

<210> SEQ ID NO 9
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA

<400> SEQUENCE: 9
ucgaccugaa caucaccau                                               19

<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA

<400> SEQUENCE: 10
auggugaugu ucaggucga                                               19

<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA

<400> SEQUENCE: 11
cuuucgcaau caauuccaa                                               19

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA

<400> SEQUENCE: 12
uuggaauuga uugcgaaag                                               19
```

```
<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA

<400> SEQUENCE: 13
ccacucgacg uacuucaua                                                  19

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA

<400> SEQUENCE: 14
uaugaaguac gucgagugg                                                  19

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
ttcaccacca tggagaaggc                                                 20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
ggcatggact gtggtcatga                                                 20

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
cgatctactc gccaacacgg tg                                              22

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
gaacgcggaa cagggcaaac ag                                              22

<210> SEQ ID NO 19
```

-continued

```
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
tcgctggagt ccaccttcga ac                                                  22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
cgaactcgtg ctccacacat cg                                                  22

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
caaagacgtg accgtgtcgc ag                                                  22

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
gcggtggtct ccatgttgtt cc                                                  22

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23
gccaggagat ggacgtgttt cg                                                  22

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
cgcgctgttc atcgttccga ag                                                  22

<210> SEQ ID NO 25
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      Primer

<400> SEQUENCE: 25
tttgcccaga ctcgagctcc tg                                              22

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
gggtgcaggt tcgggattca ac                                              22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27
ggaggttgca gtgccaacga ag                                              22

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
tggaagggag gcagggcata ac                                              22

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 29
ctggagcagc tgaatggaaa g                                               21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 30
cttgaagtcc gccctgtagg t                                               21

<210> SEQ ID NO 31
<211> LENGTH: 9
<212> TYPE: PRT
<213> ORGANISM: Human immunodeficiency virus
```

-continued

```
<400> SEQUENCE: 31

Arg Lys Lys Arg Arg Gln Arg Arg
1               5

<210> SEQ ID NO 32
<211> LENGTH: 13
<212> TYPE: PRT
<213> ORGANISM: Human immunodeficiency virus

<400> SEQUENCE: 32

Gly Arg Lys Lys Arg Arg Gln Arg Arg Thr Pro Gln
1               5                   10

<210> SEQ ID NO 33
<211> LENGTH: 11
<212> TYPE: PRT
<213> ORGANISM: Human immunodeficiency virus

<400> SEQUENCE: 33

Tyr Gly Arg Lys Lys Arg Arg Gln Arg Arg
1               5                   10

<210> SEQ ID NO 34
<211> LENGTH: 26
<212> TYPE: PRT
<213> ORGANISM: Homo sapiens

<400> SEQUENCE: 34

Ala Ala Val Ala Leu Leu Pro Ala Val Leu Leu Ala Leu Leu Ala Pro
1               5                   10                  15

Val Gln Arg Lys Arg Gln Lys Leu Met Pro
            20                  25

<210> SEQ ID NO 35
<211> LENGTH: 17
<212> TYPE: PRT
<213> ORGANISM: Caiman crocodilus

<400> SEQUENCE: 35

Met Gly Leu Gly Leu His Leu Leu Val Leu Ala Ala Ala Leu Gln Gly
1               5                   10                  15

Ala

<210> SEQ ID NO 36
<211> LENGTH: 23
<212> TYPE: PRT
<213> ORGANISM: Human immunodeficiency virus

<400> SEQUENCE: 36

Gly Ala Leu Phe Leu Gly Phe Leu Gly Ala Ala Gly Ser Thr Met Gly
1               5                   10                  15

Ala Pro Lys Ser Lys Arg Lys
            20

<210> SEQ ID NO 37
<211> LENGTH: 16
<212> TYPE: PRT
<213> ORGANISM: Drosophila sp.

<400> SEQUENCE: 37

Arg Gln Ile Lys Ile Trp Phe Gln Asn Arg Arg Met Lys Trp Lys Lys
1               5                   10                  15
```

```
<210> SEQ ID NO 38
<211> LENGTH: 5
<212> TYPE: PRT
<213> ORGANISM: Unknown Organism
<220> FEATURE:
<223> OTHER INFORMATION: Description of Unknown Organism: RGD consensus
      Peptide of unknown origin
<220> FEATURE:
<221> NAME/KEY: MOD_RES
<222> LOCATION: (1)
<223> OTHER INFORMATION: variable residue
<220> FEATURE:
<221> NAME/KEY: MOD_RES
<222> LOCATION: (5)
<223> OTHER INFORMATION: variable residue

<400> SEQUENCE: 38

Xaa Arg Gly Asp Xaa
 1               5

<210> SEQ ID NO 39
<211> LENGTH: 24
<212> TYPE: PRT
<213> ORGANISM: Influenza virus

<400> SEQUENCE: 39

Gly Leu Phe Glu Ala Ile Ala Gly Phe Ile Glu Asn Gly Trp Glu Gly
 1               5                  10                  15

Met Ile Asp Gly Gly Gly Tyr Cys
            20

<210> SEQ ID NO 40
<211> LENGTH: 27
<212> TYPE: PRT
<213> ORGANISM: Unknown Organism
<220> FEATURE:
<223> OTHER INFORMATION: Description of Unknown Organism: Transportan A
      peptide of unknown origin

<400> SEQUENCE: 40

Gly Trp Thr Leu Asn Ser Ala Gly Tyr Leu Leu Gly Lys Ile Asn Leu
 1               5                  10                  15

Lys Ala Leu Ala Ala Leu Ala Lys Lys Ile Leu
            20                  25

<210> SEQ ID NO 41
<211> LENGTH: 9
<212> TYPE: PRT
<213> ORGANISM: Unknown Organism
<220> FEATURE:
<223> OTHER INFORMATION: Description of Unknown Organism: Pre-S-peptide
      of unknown origin
<220> FEATURE:
<221> NAME/KEY: MOD_RES
<222> LOCATION: (1)
<223> OTHER INFORMATION: optional Serine for coupling

<400> SEQUENCE: 41

Ser Asp His Gln Leu Asn Pro Ala Phe
 1               5

<210> SEQ ID NO 42
<211> LENGTH: 9
<212> TYPE: PRT
<213> ORGANISM: Unknown Organism
<220> FEATURE:
<223> OTHER INFORMATION: Description of Unknown Organism: Somatostatin
      (tyr-3-octreotate) peptide of unknown origin
<220> FEATURE:
<221> NAME/KEY: MOD_RES
```

```
<222> LOCATION: (1)
<223> OTHER INFORMATION: optional Serine for coupling

<400> SEQUENCE: 42

Ser Phe Cys Tyr Trp Lys Thr Cys Thr
 1               5

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Consensus
      siRNA oligonucleotide
<220> FEATURE:
<221> NAME/KEY: modified_base
<222> LOCATION: (3)..(21)
<223> OTHER INFORMATION: a, t, c, g

<400> SEQUENCE: 43
aannnnnnnn nnnnnnnnnn naa                                          23

<210> SEQ ID NO 44
<211> LENGTH: 19
<212> TYPE: DNA
<213> ORGANISM: Unknown Organism
<220> FEATURE:
<223> OTHER INFORMATION: Description of Unknown Organism: Target
      sequence of variable origin

<400> SEQUENCE: 44
ctacggcatc agctccaaa                                               19

<210> SEQ ID NO 45
<211> LENGTH: 19
<212> TYPE: DNA
<213> ORGANISM: Unknown Organism
<220> FEATURE:
<223> OTHER INFORMATION: Description of Unknown Organism: Target
      sequence of variable origin

<400> SEQUENCE: 45
tgtggtcatt gtctattaa                                               19

<210> SEQ ID NO 46
<211> LENGTH: 19
<212> TYPE: DNA
<213> ORGANISM: Unknown Organism
<220> FEATURE:
<223> OTHER INFORMATION: Description of Unknown Organism: Target
      sequence of variable origin

<400> SEQUENCE: 46
gtttacgtat aaccacata                                               19

<210> SEQ ID NO 47
<211> LENGTH: 19
<212> TYPE: DNA
<213> ORGANISM: Unknown Organism
<220> FEATURE:
<223> OTHER INFORMATION: Description of Unknown Organism: Target
      sequence of variable origin

<400> SEQUENCE: 47
acgtgatcgt gcagaactc                                               19

<210> SEQ ID NO 48
<211> LENGTH: 19
```

```
<212> TYPE: DNA
<213> ORGANISM: Unknown Organism
<220> FEATURE:
<223> OTHER INFORMATION: Description of Unknown Organism: Target
      sequence of variable origin

<400> SEQUENCE: 48
tcgacctgaa catcaccat                                                   19

<210> SEQ ID NO 49
<211> LENGTH: 19
<212> TYPE: DNA
<213> ORGANISM: Unknown Organism
<220> FEATURE:
<223> OTHER INFORMATION: Description of Unknown Organism: Target
      sequence of variable origin

<400> SEQUENCE: 49
ctttcgcaat caattccaa                                                   19

<210> SEQ ID NO 50
<211> LENGTH: 19
<212> TYPE: DNA
<213> ORGANISM: Unknown Organism
<220> FEATURE:
<223> OTHER INFORMATION: Description of Unknown Organism: Target
      sequence of variable origin

<400> SEQUENCE: 50
ccactcgacg tacttcata                                                   19
```